United States Patent [19]

Jirkovsky et al.

[11] Patent Number: 4,665,183

[45] Date of Patent: May 12, 1987

[54] PROCESS FOR PREPARING 6,7,8,9-TETRAHYDRO-10-METHYL-PYRIDO[1,2-A]INDOL-9-AMINES AND DERIVATIVES THEREOF USEFUL FOR THE TREATMENT OF COGNITIVE IMPAIRMENTS

[75] Inventors: Ivo Jirkovsky, Plainsboro; Gary King, Lawrenceville, both of N.J.; Reinhardt Baudy, Yardley, Pa.; Victor DeNoble, Hamilton, N.J.

[73] Assignee: American Home Products Corp., New York, N.Y.

[21] Appl. No.: 888,318

[22] Filed: Jul. 18, 1986

Related U.S. Application Data

[62] Division of Ser. No. 811,551, Dec. 20, 1985.

[51] Int. Cl.$^4$ ............................................ C07D 471/04
[52] U.S. Cl. ...................................................... 546/94
[58] Field of Search ........................... 546/94; 544/126

[56] References Cited

U.S. PATENT DOCUMENTS

| | | | |
|---|---|---|---|
| 4,035,370 | 7/1977 | Lorincz et al. | 546/51 |
| 4,200,638 | 4/1980 | Hannart | 546/66 |
| 4,366,157 | 12/1982 | Ono | 546/51 |
| 4,482,714 | 11/1984 | Santroch | 544/343 |
| 4,503,058 | 3/1985 | Bertin | 544/66 |
| 4,565,872 | 1/1986 | Leir | 546/94 |

FOREIGN PATENT DOCUMENTS

| | | | |
|---|---|---|---|
| 79411 | 11/1981 | European Pat. Off. | 546/66 |
| 86416 | 2/1983 | European Pat. Off. | 546/66 |

Primary Examiner—Henry R. Jiles
Assistant Examiner—J. Richter
Attorney, Agent, or Firm—Walter Patton

[57] ABSTRACT

Herein is disclosed 6,7,8,9-tetrahydro-10-methyl-pyrido[1,2-a]indol-9-amines and derivatives, therapeutically acceptable acid addition salts thereof, processes for their preparation, methods of using the derivatives and pharmaceutical compositions. The derivatives are chemically novel agents with cerebroactive and cognition activating properties.

4 Claims, No Drawings

PROCESS FOR PREPARING 6,7,8,9-TETRAHYDRO-10-METHYLPYRIDO[1,2-A]INDOL-9-AMINES AND DERIVATIVES THEREOF USEFUL FOR THE TREATMENT OF COGNITIVE IMPAIRMENTS

This is a division of copending application Ser. No. 811,551 filed Dec. 20, 1985.

BACKGROUND OF THE INVENTION

This invention relates to novel 6,7,8,9-tetrahydro-10-methylpyrido[1,2-a]indol-9-amines and derivatives thereof, to therapeutically acceptable acid addition salts thereof, to processes for their preparation, to methods of using the derivatives and to pharmaceutical compositions of the derivatives. These derivatives have cerebroactive and cognition activating properties.

SUMMARY OF THE INVENTION

The compounds of this invention are represented by formula I

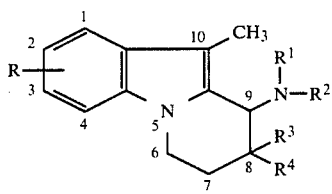

wherein R is hydrogen, lower alkyl, halogen, alkoxy containing 1 to 4 carbon atoms, hydroxy, $R^1$ and $R^2$ are independently selected from the group consisting of hydrogen, lower alkyl, cycloalkyl containing 3 to 7 carbon atoms, alkynyl containing 2 to 4 carbon atoms or $R_1$ and $R_2$ are joined together to form a heterocyclic amine radical, selected from the group consisting of pyrrolidinyl, piperidinyl and morpholinyl, and $R^3$ and $R^4$ represent hydrogen, lower alkyl, or alkenyl, wherein lower alkyl and lower alkenyl contain 1 to 4 carbon atoms, and the pharmaceutically acceptable acid addition salts thereof.

A preferred group of compounds of this invention is represented by formula I in which R is hydrogen, 2-bromo, 2- or 3-methoxy, hydroxy, $R^1$ and $R^2$ are independently hydrogen, methyl, ethyl, propyl, isopropyl, cyclopentyl, propargyl or $R^1$ and $R^2$ are joined together to form pyrrolidinyl, piperidinyl or morpholinyl, $R^3$ and $R_4$ are independently hydrogen, methyl, ethyl, propyl, propenyl and the pharmaceutically acceptable acid addition salts thereof.

A still further preferred group of compounds of this invention is represented by formula I in which R is hydrogen, 2-bromo, 2- or 3-methoxy, $R^1$ and $R^2$ are hydrogen, methyl, cyclopentyl, propargyl or $R^1$ and $R^2$ are joined together to form a heterocyclic ring, selected from the group consisting of pyrrolidinyl, piperidinyl, and morpholinyl, $R^3$ and $R^4$ are hydrogen, methyl or ethyl and the pharmaceutically acceptable acid addition salts thereof.

Compounds of formula I wherein the 10-methyl group was replaced by a larger alkyl group, such as ethyl, showed a decrease in activity. Compounds of formula I wherein $R^2$ is $-CH_2-COOC_2H_5$ or p-fluorobenzyl were also prepared and tested but showed very little activity.

The compounds of formula I or a therapeutically acceptable acid addition salt thereof can be prepared by scheme 1 or 2 set forth herein.

Scheme 1 is preferred for those compounds of formula I wherein $R^3$ and $R^4$ are other than hydrogen. When $R^3$ and $R^4$ are hydrogen, activated esters of compound VII tend to eliminate and form a double bond at position 8-9. When $R^3$ and $R^4$ are hydrogen, scheme 2 is preferred, in some cases.

Both scheme 1 and 2 utilize the intermediate ketone V (prepared according to the process of U.S. Pat. Nos. 4,482,714 and 4,515,949):

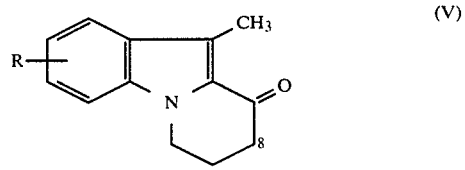

wherein R is as defined herein.

In scheme 1, the ketone V is alkylated at position 8. The ketone group of the resulting 8-dialkyl compound is reduced to the corresponding alcohol. Conversion of the 9-hydroxy group to the mesylate, tosylate or chloride and treatment with amine $R^1R^2NH$, wherein $R^1$ and $R^2$ are as defined above results in the desired compound I.

In scheme 2 the same ketone V is treated with hydroxylamine to produce the 9-oxime. Reduction of the 9-oxime results in the versatile 9-amine intermediate (X).

Direct alkylation of the 9-amine group produces compounds of formula I wherein $R^1$ and $R^2$ are the identical alkyl group.

Alternately the 9-amine compound (X) may be used for reductive amination of a carbonyl compound (i.e. an aldehyde or a ketone such as acetone or cyclopentanone) using sodium borohydride or catalytic hydrogenation.

The primary use of the 9-amine compound (X) is to subject it to a series of steps such as (g) acylating, (k) alkylating, (j) reducing; or (q) acylating, (h) reducing, (i) acylating and (j) reducing to produce compounds of formula I wherein $R^3$ and $R^4$ are hydrogen.

The compounds of formula I can be reacted with a therapeutically acceptable acid to obtain the corresponding compound of formula I as the salt with the therapeutically acceptable acid.

A pharmaceutical composition is provided by combining the compound of formula I, or a therapeutically acceptable acid addition salt thereof, and a pharmaceutically acceptable carrier.

The compounds of this invention have cerebroactive and cognitive activating properties which can be used to treat a variety of learning, memory and attentional disorders in mammals by administering to the mammal with or without cerebral ischemia an effective amount of a compound of formula I or a therapeutically acceptable acid addition salt thereof.

DETAILED DESCRIPTION OF THE INVENTION

The term "lower alkyl" as used herein means straight and branched chain alkyl radicals containing from one to four carbon atoms, and includes methyl, ethyl, propyl, 1-methylethyl, butyl, 1,1-dimethylethyl, and the like, unless stated otherwise.

The term "halogen" as used herein means halogen radicals and includes fluoro, chloro, bromo and iodo, unless stated otherwise.

The term "lower alkoxy" as used herein means straight chain alkoxy radicals containing from one to four carbon atoms and branched chain alkoxy radicals containing three to four carbon atoms and includes methoxy, ethoxy, 1-methylethoxy, butoxy and the like.

The term "lower alkenyl" as used herein means straight chain alkenyl radicals containing from two to four carbon atoms and branched chain alkenyl radicals containing three to four carbon atoms and includes ethenyl, 2-methyl-2-propenyl and the like.

The term "alkynyl" as used herein means straight chain alkynyl radicals containing from two to four carbon atoms and includes ethynyl, 2-propynyl, 1-methyl-2-propynyl and the like.

The term "cycloalkyl" as used herein means saturated cyclic hydrocarbon radicals containing from three to seven carbon atoms and includes cyclobutyl, cyclopentyl and cyclohexyl.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol diethyl ether mixture.

These salts, when administered to a mammal, possess the same or improved pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. ascorbic, citric, lactic, aspartic or tartaric acid or their aqueous solutions whose pH has been adjusted to 5.5 or less; and acids which are sparingly soluble in body fluids and which impart slow-release properties to their respective salts, e.g. pamoic or tannic acid or carboxymethyl cellulose. The preferred salt is the hydrochloride salt. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The compounds of formula I are chemically novel agents with cerebroactive and cognition activating properties. They protect against anoxia-induced lethality in mice, and have also been shown to protect against experimentally-induced learning impairments, and to promote memory retrieval, and to enhance the rate of learning in rats. Compounds of formula I enhance vigilance in rats, as indicated by changes in the electrocorticogram. At the same time compounds of formula I are free from undesireable psychostimulating side effects.

COGNITION ACTIVATING PROPERTIES

Cognition (i.e., intellectual and memory function) is difficult to define in experimental terms and particularly so in preclinical pharmacological models. In attempts to measure the cognition activating properties of the compounds of formula I in rodents, the compounds have been investigated for their ability to protect against the physical consequences of anoxia, and to correct impaired memory in simple learning tests.

To test the protective ability of the compounds of formula I against the physical consequences of anoxia, mice were exposed to an atmosphere of pure nitrogen which killed all of the animals. Intraperitoneal pretreatment of mice with the compounds of formula I protected them against this lethal effect.

The data from this anoxia-induced lethality experiment demonstrates that compounds of formula I protect the brain against the consequences of anoxia.

The passive avoidance test is a simple model of memory performance that can be used to investigate the effect of various pharmacological and pathological manipulations. In the test, a rat must remember to avoid a darkened enclosure where it had been shocked the previous day. The anticholinergic drug, scopolamine, which is known to produce memory deficits in animals and humans, impairs the rat's ability to remember to avoid the darkened enclosure. Pretreatment with compounds of formula I has been shown in this test to prevent the memory impairment caused by scopolamine. The compounds produced a dose-related protection.

A more complex model of learning and memory involved repeated testing of rats for several weeks and measurement of performance improvement rate. The animals were trained to perform a lever pressing task involving the depression of alternate levers for food. The time between the alternation response increased as testing progressed, so that the test became an increasingly difficult challenge of learning and memory. Animals treated daily with the compounds of formula I performed the alternation task with more accuracy and learned variations of the task at a faster rate than did vehicle-treated rats. This result is interpreted as indicating that the compounds of formula I enhance the rate of learning and the efficacy of memory retrieval.

To further define a central effect of the compounds of formula I, the electroencephalogram was recorded from conscious rats. The compounds of formula I had no effect on the basic rhythm of the resting electrocortical activity; however, the ratio of the power in the alpha:delta frequency range, (this ratio is an index of cortical synchronization and vigilance), tended to increase.

Collectively, experiments designed to investigate the congnition activating properties of compounds of formula I have shown these compounds to protect animals from pathological consequences of anoxia, and to prevent the effects of memory-impairing drugs.

CLINICAL UTILITY

The preclinical pharmacologic profile of the compounds of formula I suggests them to be novel and useful cognition activating agents. Therefore they are useful in the clinical treatment of a variety of learning, memory, and attentional disorders such as, minor impairments of memory fairly common with advancing age, and more fundamental cognitive changes associated with stroke, trauma, transient ischemic attacks, multi-infarct dementia, delirium, dementia, Alzheimer's disease, senile dementia of the Alzheimer's type (SDAT), amnestic syndromes, intoxication and withdrawal. Compounds of formula I are useful in the treatment of cognitive impairment in Parkinsonian and schizophrenic patients (referred to as subcortical dementias), although in these instances the dementia is perhaps secondary to a primary neurological defect. In children and young adults, treatment of dyslexia and attentional deficit disorder (ADD) may be enhanced by agents with the pharmacologic properties of the compounds of formula I. Cognitive deficits in youngsters with mental deficits secondary to cerebral anoxia at birth e.g. cerebral palsy may be treated with compounds of formula I. Cognitive deficits resulting from fetal alcohol syndrome may also respond to treatment with compounds of formula I.

Clinical evidence and laboratory studies suggest that the cognitive defects of Alzheimer's disease are due, in part, to a loss of functioning of cholinergic neurons in the brain. As disclosed, compounds of formula I prevent behavioral impairment by the cholinergic receptor antagonist scopolamine. Thus, compounds of formula I are useful as protection against at least some of the behavioral effects produced by a hypofunctioning cholinergic state.

The useful dose range of the compounds of structure I in humans is in the range of about 1 to 300 mg/day taken in one or several doses.

The compounds of formula I of this invention are used alone or in combination with pharmacologically acceptable carriers, the proportion of which is determined by the solubility and chemical nature of the compound, chosen route of administration and and standard medical practice. For example, they are administered orally in the form of capsules, tablets, suspensions or solutions or they may be injected parenterally. Capsules and tablets are the preferred mode of administration. For parenteral administration they can be used in the form of a sterile solution containing other solutes, for example, enough saline or glucose to make the solution isotonic.

The capsule and tablet compositions contain the active ingredient in admixture with non-toxic pharmaceutical excipients known to be suitable in the manufacture of capsules and tablets. Suitable pharmaceutical excipients are, for example, starch, milk, sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil for example, arachis oil, olive oil, sesame oil, or coconut oil, or in mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as cerebroactive and cognition activating agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective amount of the compounds for oral administration can usually range from about 1 to 300 mg/day in single or divided doses although as aforementioned variations will occur. However, a dosage level that is in the range of from about 1 to 150 mg/day in single or divided doses is employed most desirably for oral administration in order to achieve effective results.

The compounds of formula I also can be used to produce beneficial effects in the treatment of affective disorders, subcortical dementias, and related disorders when combined with a second therapeutic agent comprising a therapeutically effective amount of antidepressant, anxiolytic, anti-parkinsonism or neuroleptic compound commonly used as psychotherapeutic agent.

The compounds of formula I are prepared in the following manner.

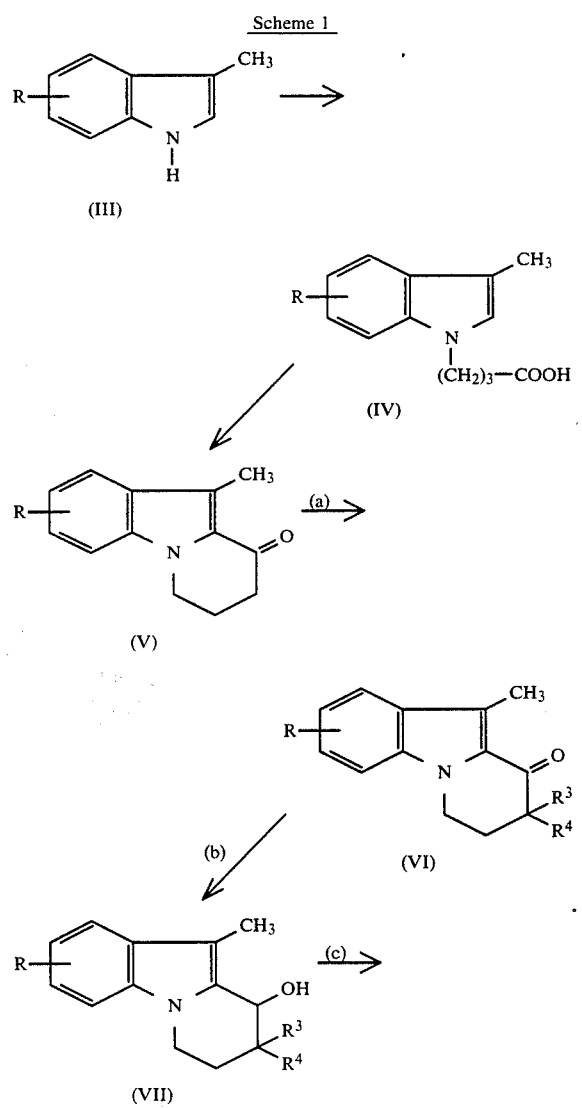

-continued
Scheme 1

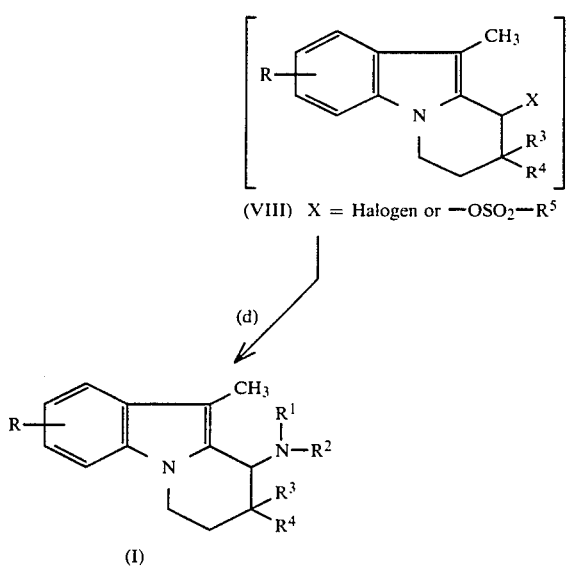

Reaction scheme 1 illustrates a method for preparing some of the compounds of formula I wherein $R^3$ and $R^4$ are both not hydrogen.

With reference to reaction scheme 1, an indole of formula III in which R is as defined herein, is condensed with γ-butyrolactone to obtain the corresponding acid of formula IV in which R is as defined herein. In this condensation, the indole of formula III is first reacted with about one molar equivalent of sodium hydride at about 100° C. to generate the anion of the compound of formula III. A solution of the anion in an inert organic solvent, preferably dimethylformamide, is mixed with about two molar equivalents of γ-butyrolactone. The resulting solution is maintained at about 130° to 160° C. for about five to ten hours, and the corresponding acid of formula IV is isolated.

Alternatively, the indole of formula III is condensed with γ-butyrolactone by refluxing in dimethylacetamide or dimethylformamide, in the presence of potassium carbonate.

Dehydrative cyclization of the acid of formula IV in which R is as defined herein gives the corresponding tricyclic ketone of formula V in which R is as defined herein. Preferred conditions for the cyclization involve reacting the acid of formula IV with an excess of a dehydrating agent, preferably polyphosphoric acid, which can also act as the solvent, at about 80° to 120° C. for about 30 minutes to 5 hours.

The tricyclic ketone of formula V is dialkylated at the 8-position (step a) with an alkyl halogenide in the presence of sodium hydride in dimethylformamide or potassium t-butoxide in t-butanol. The resulting 8,8-dialkyl-9-ketone VI, in which R, $R^3$ and $R^4$ are as defined herein, is reduced (step b) with sodium borohydride in methanol or lithium aluminum hydride in tetrahydrofuran to produce the 8,8-dialkyl-9-ol compound VII, in which R, $R^3$ and $R^4$ are as defined herein. The compound VII is treated with mesyl, tosyl or thionyl chloride in an organic base such as pyridine or triethylamine (step c). The resulting mesylate, tosylate or chloride compound VIII wherein R, $R^3$ and $R^4$ are as defined herein and X is halogen or $-OSO_2-R^5$ wherein $R^5$ is methyl or p-methylphenyl. The compound VIII is reacted, without isolation, with the amine $HNR^1R^2$ in which $R^1$ and $R^2$ are as defined herein to produce the desired compound I in which R, $R^1$-$R^4$ are as defined herein.

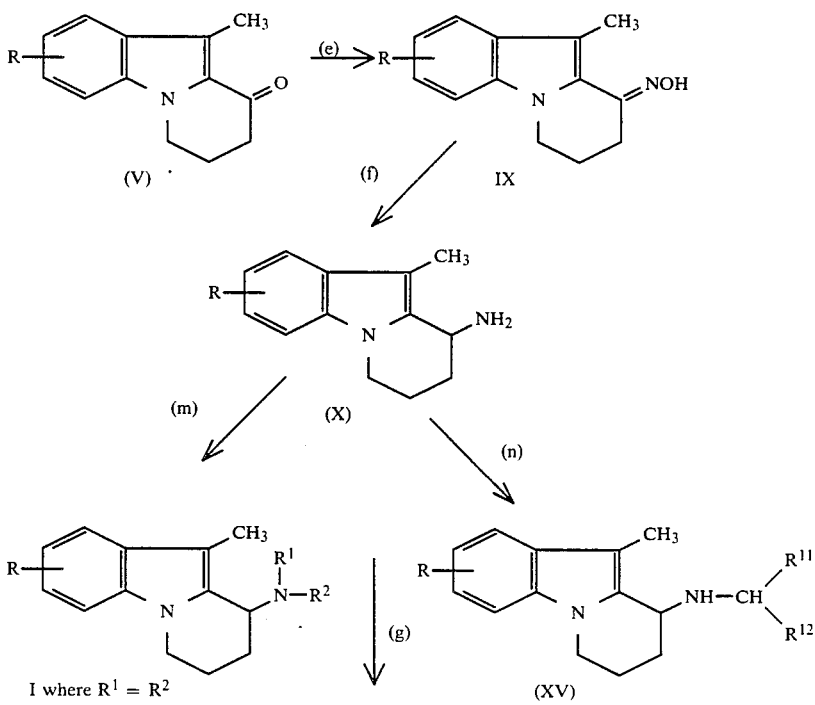

Scheme 2

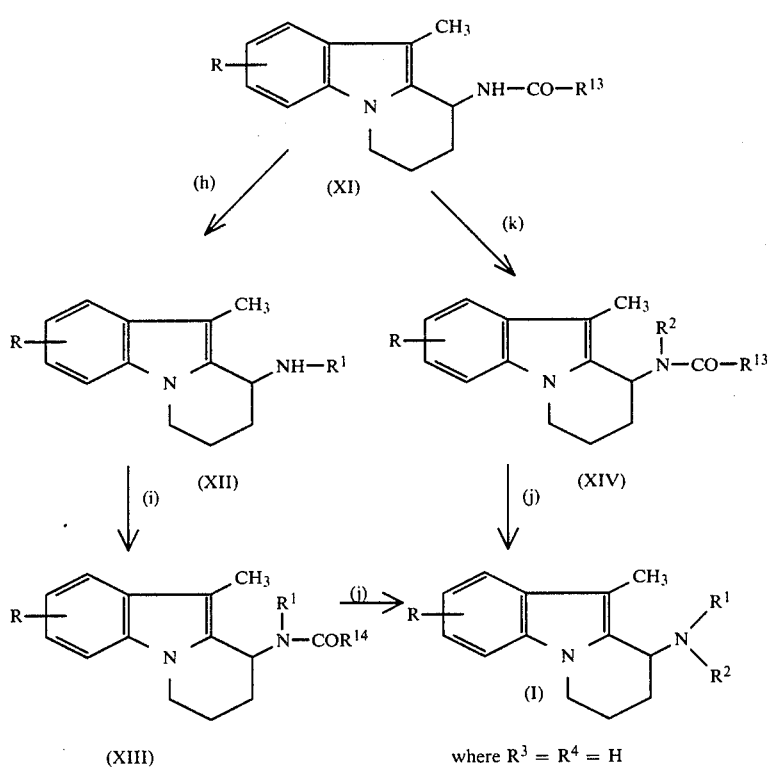

Reaction scheme 2 illustrates a method for preparing some of the compounds of formula I wherein $R^3$ and $R^4$ are both hydrogen.

In reference to scheme 2, treatment of the ketone V wherein R is as defined herein (having no substituents other than hydrogen at the 8-position) with two equivalents of hydroxylamine hydrochloride in pyridine (step e) produces the 9-oxime IX. The oxime is reduced (step f) with Raney-alloy in the presence of sodium hydroxide to produce the primary amine X. Direct alkylation of the primary amine using alkyl halogenides or dialkyl sulfates produces desired compounds of formula I wherein R is as defined herein and $R^1$ and $R^2$ are the same lower alkyl and $R^3$ and $R^4$ are both hydrogen.

Alternatively, the primary amine X may be used for the reductive amination (step n) of a carbonyl compound (aldehyde or ketone) using sodium borohydride or catalytic hydrogenation to produce the compound XV, wherein $R^{11}$—CH—$R^{12}$ represents $R^1$ or $R^2$ in formula I wherein $R^1$ or $R^2$ are selected from the values lower alkyl containing 1 to 4 carbon atoms or cycloalkyl containing 3 to 7 carbon atoms. For example, reductive amination of acetone with compound X produces compound XV wherein $R^{11}$ and $R^{12}$ are both methyl (i.e. compound I wherein $R^1$=H and $R^2$=—CH(CH$_3$)CH$_3$). In a similar manner, reductive amination of cyclopentanone with compound X produces the compound XV wherein $R^{11}$ and $R^{12}$ are joined together with —CH to form the cyclopentyl radical. This compound represents the compound of formula I wherein $R^1$=H and $R^2$ is cyclopentyl.

Further, the primary amine X is acylated (step g) to produce the N-acyl compound XI wherein $R^{13}$ is hydrogen or lower alkyl. $R^{13}$ is selected to make —CH$_2$—$R^{13}$ equal to $R^1$.

The compound XI is converted to the desired compound I by two alternate routes. One such route is represented by steps (h), (i) and (j). Reduction of compound XI with lithium aluminum hydride in benzene or tetrahydrofuran (step h) produces the secondary amine XII. Compound XII corresponds to compounds of formula I wherein R and $R^1$ are as defined herein and $R^2$, $R^3$ and $R^4$ are hydrogen. Acylation of compound XII using a mixed anhydride (step i) produces intermediate compound XIII wherein R, $R^1$ are as defined herein, $R^1$, $R^3$ and $R^4$ are hydrogen and $R^{14}$ is hydrogen or lower alkyl. $R^{14}$ is selected to make —CH$_2$—$R^{14}$ equal to $R^2$. Reduction of compound XIII (step j) with lithium aluminum hydride or diborane in tetrahydrofuran produces the compounds of formula I wherein R is as defined herein, $R^1$ and $R^2$ are as defined above and $R^3$ and $R^4$ are hydrogen.

The second route for converting the compound of formula XI to I is represented by steps (k) and (j). Alkylation of amides XI with alkyl halogenide in the presence of sodium hydride (step k) produces the intermediate compound XIV wherein R, $R^2$ and $R^{13}$ are as defined herein and $R^3$ and $R^4$ are hydrogen. Reduction of compound XIV (step j) with lithium aluminum hydride or diborane in tetrahydrofuran produces the compounds of formula I wherein R is as defined herein, $R^1$ and $R^2$ are as defined above and $R^3$ and $R^4$ are hydrogen.

The compounds of this invention possess an assymetric carbon atom at position 9 and thus are made as racemic mixtures. The d and l enantiomorphs in these racemic mixtures can be separated via standard techniques such as fractional crystallization with d-tartaric acid, l-tartaric acid, l-quinic acid and the like followed by basification and extraction of the active d or l enantiomorph free base.

The following examples are provided merely to illustrate the methods of preparation of the compounds of the present invention. These examples are not meant to be considered, in any way, as limitations of the breadth and scope of the present invention. The temperatures expressed in these examples are in degrees centigrade.

EXAMPLE 1

6,7,8,9-Tetrahydro-8,8,10-trimethyl-9-(1-pyrrolidinyl)-pyrido[1,2,a]indole Hydrochloride (I: R=—H, $R^1$ and $R^2$=

$R^3$ and $R^4$=—$CH_3$)

Step (1) Preparation of 4-(3-Methyl-1H-indol-1-yl)butanoic Acid (IV: R=H)

3-Methylindole (III: R=H) (13.1 g, 0.1 mol) and sodium hydride (5 g, 0.11 mol, ~50% in mineral oil) were melted together in a 3-neck round bottom flask immersed in 100° C. oil bath until evolution of hydrogen gas ceased. The mixture was cooled down and dissolved in 250 mL of dry dimethylformamide. Butyrolactone (17.2 g, 0.2 mol) was added and the solution was refluxed for 7 hours and poured on ice. The mixture was extracted with diethyl ether, and the acid was liberated with 10% hydrochloric acid solution. The mixture was extracted with diethyl ether. Evaporation of the extract gave a residue which was chromatographed on silica gel using 10% (v/v) ethyl acetate in benzene. Evaporation of the appropriate eluates gave 5.5 g of the title compound, mp 82°-84° C.

Step (2) Preparation of 6,7,8,9-Tetrahydro-10-methyl-pyrido[1,2-a]indol-9-one (V: R=H)

4-(3-Methyl-1H-indol-1-yl)butanoic acid (5 g) was suspended in polyphosphoric acid and the mixture was heated at 100° C. for 1 hour, cooled, and poured on ice. The mixture was extracted with diethyl ether. The extract was washed with 10% aqueous sodium bicarbonate, evaporated (4.4 g of crude product) and chromatographed through silica gel using 5% methanol in chloroform (v/v).

The appropriate eluates were evaporated to give the title compound, m.p. 87°-89° C.

NMR (CDCl$_3$) δ2.2 (m, 2H), 2.5 (m, 2H), 2.58 (s, 3H), 4.0 (t, 2H), 7.1 (m, 3H) and 7.4 (m, 1H);

IR (CHCl$_3$) 1648 cm$^{-1}$;

UV max (MeOH) 316 nm ($\epsilon$21611) and 241 (26009);

Anal. Calcd. for C$_{13}$H$_{13}$NO: C, 78.36%; H, 6.58%; N, 7.03% Found: C, 78.16%; H, 6.84%; N, 7.07%.

Step (3) Preparation of 6,7,8,9-Tetrahydro-8,8,10-trimethylpyrido[1,2-a]indol-9-one (VI: R=—H, $R^3$ and $R^4$=—$CH_3$)

Sodium hydride (8.5 g, 0.2 mol, ~60% in mineral oil) was added portionwise over 30 minutes to a solution of 10-methyl-6,7,8,9-tetrahydropyrido[1,2-a]indol-9-one (19.9 g, 0.1 mol) in dimethylformamide (200 mL) under exclusion of moisture. The reaction mixture was stirred at 25° C. for 1 hour. Methyl iodide (31.3 g, 0.22 mol) was added dropwise with ice water cooling over 15 minutes. After stirring at room temperature for 2 hours, the reaction mixture was evaporated in vacuo to near-dryness and the residue suspended in water (100 mL). The organic products were extracted with chloroform (4×50 mL). The combined organic layers were washed with brine (100 mL), dried over MgSO$_4$, filtered, and evaporated to dryness. The dark oily residue (25.6 g) was chromatographed on silica gel (750 g). Gravity elution with chloroform/hexane (1:1) afforded 12.94 g (57%) of the title compound. Analytical specimen was recrystallization from ether, m.p. 73°-4° C.

IR (KBr) 1655, 1530, cm$^{-1}$;

UV (MeOH) $\lambda_{max}$=241, 315.5 nm/$\epsilon$=23300, 20300 respectively;

NMR (CDCl$_3$) δ1.3 (s, 6H, $\overline{CH_3}$—C—$\overline{CH_3}$), 2.2 (t, J=7 Hz, 2H, CH$_2$), 2.68 (s, 3H, $\overline{CH_3}$) 4.23 (t, J=7 Hz, 2H, N—$\overline{CH_2}$), 7.1-7.42 (m, 3H, Ar—H), 7.71 (d, J=8, 6 Hz, 1H, $\overline{H}$-1);

MS (relative intensity, fragment) m/e 227 (100, M+), 212 (95, M-CH$_3$), 197 (5, 212-CH$_3$);

Anal. Calcd.: C, 79.26%; H, 7.54%; N, 6.16% Found: C, 79.09%; H, 7.55%; N, 6.90%.

Improved Procedure for Preparation of 6,7,8,9-tetrahydro-8,8,10-trimethylpyrido[1,2-a]indol-9-one At 60° C. a solution of 10-methyl-6,7,8,9-tetrahydropyrido[1,2-a]indole-9-one (1.99 g, 10 mmol), in t-butanol (30 mL) was added at once to a refluxing solution of potassium t-butoxide (4.48 g, 40 mmol) in the same solvent (60 mL). Immediately following, a solution of iodomethane (17 g, 120 mmol) in t-butanol (15 mL) was added dropwise to the reaction mixture at 1°-2° C. below the reflux temperature over 5–10 minutes. After stirring at reflux for 2 hours, the mixture was evaporated in vacuo to near-dryness and suspended in water (50 mL). The product was extracted with CH$_2$Cl$_2$ (3×25 mL). The combined organic layers were washed with water (2×20 mL), dried over MgSO$_4$, filtered, and evaporated in vacuo to dryness. The residue was chromatographed on silica gel (60 g). Flash elution with chloroform/hexane (1:1) afforded 1.92 g (85%) of the title compound. The product was in all spectral aspects identical to product of Step 3.

Step (4) Preparation of 6,7,8,9-Tetrahydro-8,8,10-trimethylpyrido[1,2-a]indol-9-ol (VII: R=—H, $R^3$ and $R^4$=—$CH_3$)

Sodium borohydride (3.89 g, 0.1024 mol) was added portiowise upon cooling to a solution of 6,7,8,9-tetrahydro-8,8,10-trimethylpyrido[1,2-a]indole-9-one (7.75 g, 0.0341 mol) in methanol (300 mL) at 25° C. The reaction mixture was stirred at room temperature for 14 hours. After evaporation of the mixture in vacuo to dryness, the residue was suspended in water (100 mL). The product was extracted with chloroform (3×75 mL). The combined organic layers were dried over MgSO$_4$, filtered, and evaporated to afford 7.66 g (98%) the title compound. Analytical specimen was crystallized from benzene/hexane to give a beige solid, m.p. 153°-4° C.

NMR (CDCl$_3$) δ=0.91 (s, 3H, CH$_3$—8), 1.2 (s, 3H, CH$_3$—8), 1.5-1.69 (m, 1H, H—7), 2.25-2.42 (multiplet with a singlet spike at 2.33, 4H, H—7 and CH$_3$—10), 3.73-3.92 (m, 1H, H—6), 4.12-4.25 (m, 1H, H—6), 4.57 (s, 1H, H—9), 7.08-7.37 (m, 3H, Ar—H), 7.55 (d, J=8.6 Hz, 1H, H—1);

IR (KBr) 3320 (broad), 2920, 1460, 1340 cm$^{-1}$;

UV (MeOH) $\lambda_{max}$=287.5 nm/$\epsilon$=7050.

MS (relative intensity, fragment) m/e 229 (66, M+), 214 (11, M—CH$_3$), 212 (11, M—OH).

Anal. Calcd.: C, 78.56%; H, 8.35%; N, 6.11% Found: C, 78.56%; H, 8.09%; N, 6.04%.

Step (5) Preparation of 6,7,8,9-Tetrahydro-8,8,10-trimethyl-9-(1-pyrrolidinyl)pyrido[1,2,a]indole Hydrochloride (I: R=—H, R$^1$ and R$^2$=

R$^2$ and R$^4$=—CH$_3$)

A solution of 6,7,8,9-tetrahydro-9-hydroxy-8,8,10-trimethylpyrido[1,2-a]indole (6.4 g, 27.9 mmol) in dry pyridine (100 mL) was treated with a solution of methanesulfonyl chloride (6.4 g, 55.8 mmol) in dry pyridine (5 mL) at 0° C. The reaction mixture was stirred at 0° C. for ½ hour, then at 40° C. for ½ hour. Distilled pyrrolidine (11.9 g, 167.4 mmol) was added dropwise at 25° C. over 10 minutes. The mixture was stirred at room temperature overnight, under exclusion of moisture, and evaporated to dryness in high vacuo. The residue was taken up in ether (100 mL) and extracted with 1% hydrochloric acid (3×75 mL). The combined aqueous layers were basified with saturated sodium carbonate to pH 8.5 and extracted with toluene (3×75 mL). The combined organic layers were dried over MgSO$_4$, filtered, and evaporated to afford 7.36 g, (93.5%) of the title base, m.p. 103°–104.5° C. The monohydrochloride was prepared in ethanol, and recrystallized from acetonitrile/ether (9:1) to give a white solid, m.p. 171°–172.5° C.

NMR (DMSO-d$_6$) δ0.77 and 1.44 (singlets, 3H+3H, CH$_3$—8), 2.32 (s, 3H, CH$_3$—10), 1.65-2.05 (m, 4H, CH$_2$ of pyrrolidine), 2.55, 3.05, 3.40, and 3.79 (multiplets, each 1H, CH$_2$—N of pyrrolidine), 3.64 (td, J$_{gem}$=12.2 Hz, J=5.9 Hz, 1H, H—6 ax), 4.36 (dd, J$_{gem}$=12.2 Hz, J=7.2 Hz, 1H, H—6 eq), 4.78 (bd, J=4.4 Hz, 1H, H—9), 7.1-7.6 (m, 4H, Ar—H), 9.75 (bs, 1H, NH+);

IR (KBr) 2920, 2880, 2580 (broad), 2500, 1460, 1345, 1320 cm$^{-1}$;

UV (MeOH) λ$_{max}$ 277.5 nm/ε=8227;

MS (relative intensity, fragment) m/e 282 (100, M+);

Anal. Calcd.: C, 71.56%; H, 8.53%; N, 8.78% Found: C, 71.73%; H, 8.28%; N, 8.78%.

EXAMPLE 2

6,7,8,9-Tetrahydro-10-methyl-9-(1-pyrrolidinyl)-pyrido[1,2-a]indole Hydrochloride (I: R, R$^3$, and R$^4$=—H, R$^1$ and R$^2$=

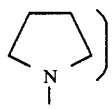

Step (1) Preparation of 6,7,8,9-Tetrahydro-10-methyl-pyrido[1,2-a]indol-9-ol
(VI: R, R$^3$, and R$^4$=H)

To a cooled solution of 10-Methyl-6,7,8,9-Tetrahydropyrido[1,2-a]indole-9-one (19.9 g, 0.1 mol, described in Example 1, Step (2) in methanol (1200 mL) was added sodium borohydride (10 g) portionwise. The reaction mixture was stirred at 25° C. for 14 hours, and evaporated in vacuo. The residue was partitioned between water (300 mL) and chloroform (400 mL), the organic layer was separated, dried (MgSO$_4$), filtered, and evaporated. The crude product was recrystallized from ether-hexane: m.p. 116°–118° C.; yield 20 g (99%).

NMR (CDCl$_3$) δ1.65 (broad, 1H, OH, exchangeable), 1.5-2.6 (m with a singlet spike at 2.32, 7H, CH$_2$ and CH$_3$), 3.72 (td, J=12 Hz, 4.5 Hz, 1H, H—6 ax), 4.20 (m, 1H, H—6 eq), 5.13 (t, J=4 Hz, 1H, H—9); 6.9-7.3 (m, 3H, Ar—H), 7.51 (doublet with fine splitting, J=8 Hz, 1H, H—1);

MS m/e (relative intensity, fragment): 201 (100, M+), 200 (40, M—1), 186 (65, M—CH$_3$), 184 (90, M—OH), 168 (20, 186—H$_2$O), * 172.1 for 201 to 186, * 168.4 for 201 to 184.

Step (2) Preparation of 6,7,8,9-Tetrahydro-10-methyl-9-(1-pyrrolidinyl)pyrido[1,2-a]indole Hydrochloride To a solution of 6,7,8,9-tetrahydro-10-methyl-pyrido[1,2-a]indol-9-ol (2.01 g, 10 mmol) in dry pyridine (100 mL) was added a solution of p-toluenesulfonyl chloride (7.6 g, 10 mmol) in the same solvent (50 mL) at 5°–10° C. Maintaining this temperature, stirring was continued for 60 minutes, and then, the reaction mixture was treated with distilled pyrrolidine (7.1 g, 100 mmol), and stirred at room temperature for 8 hours. The resultant solution was poured into ice-water, and the product was extracted with methylene chloride. The combined extracts were washed with water, dried (MgSO$_4$), filtered, and evaporated. The residue was chromatographed using methylene chloride/methanol 99:1. The title base 1.8 g (70%) was converted to the hydrochloride salt in acetonitrile with ethereal HCl, and recrystallized from ethanol, m.p. 179°–181° C. (analytical specimen m.p. 182° C.).

IR (NUJOL) 2580 cm$^{-1}$;

UV (MeOH) λ$_{max}$ 276 nm (ε=8,080), 225 nm (ε=36,700).

NMR (DMSO-d$_6$) δ2.0 (m, 5H, CH$_2$), 2.36 (s, 3H, CH$_3$), 2.75, 3.20 and 3.6 (multiplets, 8H, CH$_2$ and CH$_2$—N), 4.37 (dd, J=12 Hz, 6 Hz, 1H, H—6 eq), 4.85 (m, 1H, H—9), 7.0-7.6 (m, 4H, Ar—H), 10.8 (br, 1H, NH+);

MS, m/e (relative intensity, fragment) 254 (10, M+), 184 (100, loss of charged pyrroline), 183 (66, loss of pyrrolidine);

Anal. Calcd.: C, 70.21%; H, 7.97%; N, 9.63% Found: C, 69.90%; H, 7.87%; N, 9.53%.

EXAMPLE 3

6,7,8,9-Tetrahydro-N,N,10-trimethylpyrido[1,2-a]indole-9-amine Hydrochloride (I: R, R$^3$ and R$^4$=—H, R$^1$ and R$^2$=—CH$_3$)

A solution of 6,7,8,9-tetrahydro-10-methylpyrido[1,2-a]indol-9-ol (560 mg, 2.78 mmol, described in Example 2, Step 1), in benzene (40 mL) was treated with thionyl chloride (357 mg, 3 mmol). The reaction mixture was stirred at 25° C. for 90 minutes, and then saturated with dry dimethylamine (gas) upon ice-cooling. Stirring was continued at room temperature for 14 hours. The product was extracted with 5% hydrochloric acid. The aqueous phase was filtered, and the pH was adjusted to 8 with solid Na$_2$CO$_3$. The resultant mixture was extracted with chloroform. The combined extracts were evaporated, and the residue was purified by chromatography on silica gel. Elution with chloroform/methanol 99:1 afforded 82 mg (13%) of the title base.

NMR (CDCl$_3$) δ2.28 and 2.32 (singlets, 6H+3H, CH$_3$);

MS, m/e (relative intensity, fragment) 228 (30, M+), 213 (1, M—CH$_3$), 185 (40, 213-ethylene), 184 (100, loss of CH$_2$=NH—CH$_3$), 183 (80, M-dimethylamine), 169 (40, 184—CH$_3$), * 146.9 for 228 to 183, * 155.2 for 184 to 169.

The corresponding hydrochloride salt was crystallized from methanol-ether, m.p. 166°–168° C.

IR (CHCl$_3$) 2500 cm$^{-1}$;

UV (MeOH) λ$_{max}$ 276 nm (ε=8,200), 226 nm (ε=35,800);

NMR (CDCl$_3$) δ2.05 (m, 4H, CH$_2$), 2.35 (s, 3H, CH$_3$), 2.57 and 2.94 (doublets, J=5.5 Hz, 6H, CH$_3$—N), 3.73 (td, J=11.5 Hz and 5 Hz, 1H, CH$_2$—6 ax), 4.32 (m, 1H, CH$_2$—6 eq), 4.53 (m, 1H, H—9), 7.25 (m, 3H, ArH), 7.52 (m, 1H, H—1), 11.23 (br, 1H, NH+);

MS m/e (relative intensity, fragment) 228 (30, M+), 184 (100, loss of CH$_2$=N+H—CH$_3$), 183 (95, loss of dimethylamine), 169 (40, 184—CH$_3$), 168 (35, 183—CH$_3$), * 146.88 for 228 to 183;

Anal. Calcd.: C, 68.03%; H, 7.99%; N, 10.58% Found: C, 67.76%; H, 7.84%; N, 10.46%.

EXAMPLE 4

6,7,8,9-Tetrahydro-N,N,8,8,10-pentamethylpyrido[1,2-a]indol-9-amine Hydrobromide (I: R=—H, R$^1$, R$^2$, R$^3$, R$^4$=—CH$_3$)

A solution of the starting alcohol (458 mg, 2 mmol, described in Example 1, Step 4) in dry pyridine (20 mL) was treated with a solution of tosyl chloride (420 mg, 2.2 mmol) in dry pyridine (5 mL) at 0° C. The reaction mixture was stirred at 50°–60° C. for 20 hours. Additional tosyl chloride (191 mg, 1 mmol) was added to the reaction mixture and stirring continued at ~50° C. for 36 hours. After cooling the mixture to 0° C., anhydrous dimethylamine was introduced upon ice cooling until saturation. After stirring for an additional 24 hours at 25° C., the reaction mixture was evaporated to dryness in vacuo. The residue was repeatedly evaporated with 2% MeOH in CHCl$_3$ afforded 363 mg (71%) of the title base. The monohydrobromide salt was prepared in ether with 0.95 equivalent of HBr in methanol, and triturated from ether, m.p. 139°–141° C.

IR (KBN) 3440 (broad, 2920 (broad), 2700 (broad), 1460, 1350, 1135 cm$^{-1}$;

UV (MeOH) λ$_{max}$ 277.5/ε=8319;

NMR (DMSO-d$_6$) δ0.83 (s, 3H, CH$_3$—8), 1.54 (s, 3H, CH$_3$—8), 2.39 (s, 3H, CH$_3$—10), 3.48 (s, 6H, CH$_3$—N—CH$_3$), 3.62–3.92 (m, 1H, H—6), 4.16–4.65 (m, 1H, H—6), 4.9 (br s, 1H, H9), 7.12–7.8 (m, 4H, Ar—H), 9.1 (br s, 1H, NH);

MS (relative intensity, fragment) m/e 256 (11, M+), 212 (100, loss of CH$_2$=N+H—CH$_3$), 197 (36,212—CH$_3$);

Anal. Calcd.: C, 60.54%; H, 7.47%; N, 8.30% Found: C, 60.55%; H, 7.50%; N, 8.31%.

EXAMPLE 5

8,8-Diethyl-6,7,8,9-tetrahydro-N,N-10-trimethylpyrido[1,2-a]indol-9-amine Hydrochloride (I: R=—H, R$^1$ and R$^2$=—CH$_3$, R$^3$ and R$^4$=—C$_2$H$_5$)

Step (1) Preparation of 8,8-Diethyl-6,7,8,9-tetrahydro-10-methylpyrido[1,2-a]indol-9-one Sodium hydride (850 mg, 20 mmol, ~60% in mineral oil) was added portionwise over 3 minutes to a solution of 10-methyl-6,7,8,9-tetrahydropyrido[1,2-a]indole-9-one (1.99 g, 10 mmol, described in Example 1, Step (2), in dimethylformamide (20 mL) under exclusion of moisture. The reaction mixture was stirred at 25° C. for 1 hour. Ethyl iodide (3.43 g, 22 mmol) was added dropwise over 5 minutes. After stirring at 60° C. for 2 hours, the mixture was evaporated in vacuo to near-dryness and the residue suspended in water (50 mL). The organic products were extracted with ether (3×50 mL). The combined organic layers were washed with both 5% hydrochloride acid and 10% sodium bicarbonate (3×50 mL). The organic layer was dried over MgSO$_4$, filtered and evaporated to dryness. The dark oily residue was chromatographed on silica gel (80 g). Flash elution with hexane/chloroform (75:25) afforded 1.7 g (67%) of the title compound as a yellow oil.

NMR (CDCl$_3$) δ0.83 (t, J=7 Hz, 6H, 2CH$_3$ of ethyl), 1.71 (q, J=7 Hz, 4H, 2CH$_2$ of ethyl), 2.18 (t, J=6 Hz, 2H, CH$_2$—7), 2.65 (s, 3H, CH$_3$), 4.21 (t, J=6 Hz, 2H, CH$_2$—6), 6.98-7.45 (m, 3H, Ar—H), 7.74 (dd, J=1.8 Hz, 1H, H—1);

MS (relative intensity, fragment) m/e 255 (57, M+), 226 (100, M-ethyl), 198 (226-CO).

Step (2) Preparation of 8,8-Diethyl-6,7,8,9-tetrahydro-10-methylpyrido[1,2-a]indol-9-ol Sodium borohydride (19 g, 500 mmol) was added portionwise upon cooling to a solution 8,8-diethyl-6,7,8,9-tetrahydro-10-methylpyrido[1,2-a]indol-9-one (12.8 g, 50 mmol) in methanol (500 mL) at 25° C. The reaction mixture was heated at 40° C. for 18 hours. The solvent was removed in vacuo and the residue partitioned between 1% ammonium hydroxide (100 mL) and chloroform (120 mL). The separated organic layer was dried over MgSO$_4$, filtered and evaporated to afford the desired alcohol 12 g, (93%) as a greenish oil.

NMR (CDCl$_3$) δ0.82 (t, J=7 Hz, 3H, CH$_3$ of ethyl), 1.03 (t, J=7 Hz, 3H, CH$_3$, of ethyl), 1.5 (s, 1H, OH), 1.61-2.05 (m, 4H, 2CH$_2$ of ethyl), 2.3 (s, 3H, CH$_3$), 3.45-3.91 (m, 3H, Ar—H), 3.93-4.26 (m, 2H, CH$_2$—6), 4.65 (s, 1H, H—9), 7.1-7.28 (m, 3H, Ar—H), 7.41-7.67 (m, 1H, H—1);

MS (relative intensity, fragment) m/e 257 (44, M+), 228 (12, M-ethyl), 173 [100, loss of CH$_2$=C (Et)$_2$].

Reduction with LiAlH$_4$ (2 moles per 1 mole of ketone) in THF at ambient temperature for 2–12 hours gave 99% yield of 8,8-diethyl-6,7,8,9-tetrahydro-10-methylpyrido[1,2-a]indol-9-ol.

Step (3) Preparation of 8,8-Diethyl-6,7,8,9-tetrahydro-N,N-10-trimethylpyrido[1,2-a]indol-9-amine Hydrochloride A solution of 8,8-diethyl-6,7,8,9-tetrahydro-10-methylpyrido[1,2-a]indol-9-ol (3.1 g, 12 mmol) in dry pyridine (75 mL) was treated with a solution of mesyl chloride (2.8 g, 24 mmol) in the same solvent (25 mL). The reaction mixture was stirred at 40° C. for 60 minutes, cooled to 0°–5° C., saturated with dimethylamine gas, and allowed to warm to ambient temperature overnight. Pyridine was removed in vacuo, and the residue was partitioned between 5% aqueous sodium carbonate (50 mL) and methylene chloride (3×25 mL). The organic extracts were evaporated, and the oily material was partitioned between ether and 0.5N hydrochloric acid. The aqueous layer was separated, basified with a saturated solution of sodium carbonate, and extracted with ether. The combined extracts were dried (MgSO$_4$), filtered, and evaporated to dryness (2.7 g of crude product). Chromatographic purification was carried out on neutral alumina (190 g, activity III). Elution with hexane-methylene chloride 1:1 afforded 1.7 g (50% yield) of the title base. The corresponding hydrochloride salt was crystallized from acetonitrile/ether, m.p. 140°-143° C.

IR (KBr) 2970, 2940, 2890, 2560 (broad), and 1460 cm$^{-1}$;

UV (MeOH) $\lambda_{max}$ 277.5 mm ($\epsilon$=8910);

NMR (DMSO-d$_6$) δ0.72 and 0.94 (triplets, J=7.5 Hz, 3H+3H, CH$_3$ of ethyl), 1.02 (m, 2H, CH$_2$ of ethyl), 1.81 * (m, 1H, CH$_2$ of ethyl), 1.93* (overlapping multiplets, 1H+1H, CH$_2$ of ethyl and CH$_2$—7), 2.25* (m, 1H, CH$_2$—7), 2.23 and 2.95 (doublets, J=5 Hz, 3H+3H, CH$_3$—N, collapse to broad singlets upon exchange), 2.38 (s, 3H, CH$_3$), 3.68 (dt, J=6.5 Hz, J$_{gem}$=12.2 Hz, 1H, H—6 ax), 4.34 (dd, J—7.3 Hz, J$_{gem}$=12.2 Hz, 1H, H—6 eq), 4.64* (br s, 1H, H—9), 7.12 and 7.24 (triplets, J=8 Hz, 1H+1H, H—2 and H—3), 7.42 (d, J=8 Hz, 1H, H—4), 7.59 (d, J=8 Hz, 1H, H—1); *signals shift upon deuteration;

MS (relative intensity, fragment) m/e 284 (27, M$^+$), 241 (22), 240 (100, loss of CH$_3$—N+H=CH$_2$), 239 (11, loss of dimethylamine), 269 (2), 254 (1), 239 (11), 224 (12) are consecutive losses of CH$_3$), 211 (41, 240 ethyl);

Anal. Calcd.: C, 71.11%; H, 9.11%; N, 8.73% Found: C, 71.20%; H, 8.79%; N, 8.85%.

EXAMPLE 6

8,8,-Diethyl-6,7,8,9-tetrahydro-10-methyl-9-(1-pyrolidinyl)pyrido[1,2-a]indole Hydrochloride (I: R=—H, R$^1$ and R$^2$=

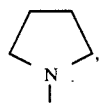

R$^3$ and R$^4$=—C$_2$H$_5$)

A solution of 8,8-diethyl-6,7,8,9-tetrahydro-10-methylpyrido[1,2-a]indol-9-ol (3.49 g, 13.6 mmol, described in Example 5, Step (2) in dry pyridine (100 mL) was treated with a solution of methanesulfonyl chloride (3.11 g, 27.2 mmol) in dry pyridine (5 mL) at 0°-5° C. The reaction mixture was stirred 1 hour at room temperature then 1 hour at 40° C. under exclusion of moisture. Distilled pyrrolidine (5.8 g, 81.6 mmol) was added in a dropwise manner at 25° C. over 5 minutes. The mixture was suspended in ether (100 mL) and extracted with 1% hydrochloric acid (3×50 mL). The separated aqueous layer was basified with saturated sodium carbonate to pH8 and extracted with toluene (3×50 mL). The combined organic layer was dried over MgSO$_4$, filtered and evaporated to dryness in vacuo to afford 2.6 g (62%) of the title base. The monohydrochloride was prepared in ethanol with ethanolic HCl, and recrystallized as white microcrystals from acetonitrile/ether (9:1), m.p. 152°-3° C.

IR (KBr) 3430 (broad), 2970, 2880, 2600, 1460, 1350, 1320, 1250 cm$^{-1}$;

UV (MeOH) $\lambda_{max}$ 277.5, 226.5 nm/$\epsilon$=8,347, 35,550 respectively;

NMR (DMSO-d$_6$) δ0.72 and 0.91 (triplets, J=7.2 Hz, 3H+3H, CH$_3$ of ethyl), 2.38 (s, 3H, CH$_3$—10), 4.78 (very narrow doublet, 1H, H—9), 7.1-7.7 (m, 4H, Ar—H), 9.91 (bs, 1H, NH$^+$);

Anal. Calcd.: C, 72.70%; H, 9.01%; N, 8.07%. Found: C, 72.79%; H, 8.90%; N, 8.09%.

EXAMPLE 7

6,7,8,9-Tetrahydro-10-methyl-N-(2-propynyl)-pyrido[1,2-a]indol-9-amine Hydrochloride (I: R, R$^1$, R$^3$ and R$^4$=—H, R$^2$=—CH$_2$—C≡CH)

To a solution of 6,7,8,9-tetrahydro-10-methylpyrido[1,2-a]indol-9-ol (2.01 g, 10 mmol, described in Example 2, Step 1) in dry pyridine (150 mL) was added a solution of p-toluenesulfonyl chloride (7.6 g, 40 mmol) in the same solvent (50 mL) at 0° C. Maintaining this temperature, stirring was continued for 60 minutes and an excess of propargylamine was added. The reaction mixture was stirred at ambient temperature for 3 hours, poured into water, and extracted with methylene chloride. The combined extracts were evaporated, and the residue was chromatographed. Elution with methylene chloride/methanol 20:1 afforded the title base. The hydrochloride salt was crystallized from methanol, m.p. 172° C.

IR (NUJOL) 3210 (NH), 2700-2400 (NH$^+$), 2130 (C≡C) cm$^{-1}$;

NMR (DMSO-d$_6$) δ2.32 (s, 3H, CH$_3$), 3.74 (m, 2H, CH$_2$—N) 4.82 (m, 1H, H—9);

MS 238 (35, M$^+$), 183 (100, loss of propargylamine);

Anal. Calcd.: C, 69.94%; H, 6.97%; N, 10.19% Found: C, 69.76%; H, 6.88%; N, 10.19%.

EXAMPLE 8

6,7,8,9-Tetrahydro-10-methyl-9-(1-piperidinyl)-pyrido[1,2-a]indole Hydrochloride (I: R, R$^3$ and R$^4$=—H, R$^1$ and R=

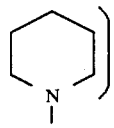

To a solution of 6,7,8,9-tetrahydro-10-methylpyrido[1,2-a]indol-9-ol (2.01 g, 10 mmol, described in Example 2, Step 1) in dry pyridine (150 mL) was added a solution of p-toluenesulfonyl chloride (7.6 g, 40 mmol) in the same solvent (50 mL) at 0° C. Maintaining this temperature, stirring was continued for 60 minutes, and an excess of piperidine was introduced. The reaction mixture was stirred at ambient temperature for 3 hours, poured into water, and extracted with methylene chloride. The combined extracts were evaporated, and the residue was chromatographed. Elution with methylene chloride/methanol 20:1 afforded the title base. The hydrochloride salt was crystallized from EtOH/water, m.p. 228°-230° C.

NMR (DMSO-d$_6$) δ2.35 (s, 3H, CH$_3$), 4.75 (b, 1H, H—9);

MS 268 (12, M$^+$), 183 (100, M-piperidine);

Anal. Calcd.: C, 70.91%; H, 8.26%; N, 9.19% Found: C, 70.98%; H, 8.27%; N, 9.23%.

EXAMPLE 9

6,7,8,9-Tetrahydro-10-methyl-9-(4-morpholinyl)-pyrido[1,2-a]indole Hydrochloride (I: R=—H, R$^1$ and R$^2$=

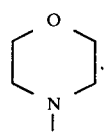

$R^3$ and $R^4$ = —H)

To a solution of 6,7,8,9-tetrahydro-10-methyl-pyrido[1,2-a]indol-9-ol (2.01 g, 10 mmol, described in Example 2, Step (1) in dry pyridine (150 mL) was added a solution of p-toluenesulfonyl chloride (7.6 g, 40 mmol) in the same solvent (50 mL) at 0° C. Maintaining this temperature, stirring was continued for 60 minutes, and an excess of morpholine was added. The reaction mixture was stirred at ambient temperature for 3 hours, poured into water, and extracted with methylene chloride. The combined extracts were evaporated, and the residue was chromatographed. Elution with methylene chloride/methanol 20:1 afforded the title base. The hydrochloride salt was crystallized from EtOH, m.p. 172°-174° C.

NMR (DMSO-$d_6$) δ2.35 (s, 3H, $CH_3$), 3.95 (m, 5H, $CH_2O$ and H—6 ax), 4.35 (m, 1H, H—6 eq), 4.82 (m, 1H, H—9);

MS 270 (40, $M^+$), 184 (100), 183 (60);

Anal. Calcd.: C, 66.54%; H, 7.56; N, 9.13%. Found: C, 66.33%; H, 7.53; N, 9.02%.

EXAMPLE 10

6,7,8,9-Tetrahydro-10-methyl-8,8-bis(2-propenyl)-9-(1-pyrrolidinyl)-pyrido[1,2-a]indole Hydrochloride (I: R—H, $R^1$ and $R^2$ =

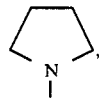

$R^3$ and $R^4$ = —$CH_2$—CH=$CH_2$)

Step (1) Preparation of 6,7,8,9-Tetrahydro-10-methyl-8,8-bis(2-propenyl)pyrido[1,2-a]indol-9-one Sodium hydride (8 g, 0.2 mol, ~60% in mineral oil) was added portionwise over 30 minutes to a solution of 10-methyl-6,7,8,9-tetrahydropyrido[1,2-a]indol-9-one (19.9 g, 0.1 mol, described in Example 1, Step 2), in dimethylformamide (200 mL) under exclusion of moisture. The reaction mixture was stirred at 25° C. for 1 hour. Allyl bromide (26.62 g, 0.22 mol) was added dropwise upon mild cooling over 20 minutes, then stirred at 25° C. overnight. The solvent was reduced in vacuo to near-dryness, and the residue partitioned between water (200 mL) and ether (200 mL). The separated organic layer was dried over $MgSO_4$, filtered and evaporated in vacuo to dryness. The dark oily residue was chromatographed on silica gel (300 g). Flask elution with chloroform/hexane (1:1) afforded 19.25 g (69%) of the title compound as a light amber oil.

NMR ($CDCl_3$) δ2.25 (t, J=6.2 Hz, 2H, $CH_2$—7), 2.47 (sym. multiplet, 4H, $CH_2$—C of allyl), 4.22 (t, J=6.2 Hz, 2H, $CH_2$—6), 5.10 (m, 4H, =$CH_2$), 5.82 (m, 2H, —CH=), 7.1-7.45 (m, 3H, Ar—H), 7.71 (d, J=8 Hz, 1H, H—1);

MS (Relative intensity, fragment) m/e 279 (55, $M^+$), 238 (100, M—$CH_2$—CH=$CH_2$).

Step (2) Preparation of 6,7,8,9-Tetrahydro-10-methyl-8,8-bis(2-propenyl)pyrido[1,2-a]indol-9-ol Sodium borohydride (10.53 g, 270 mmol) was added portionwise upon cooling to a solution of 6,7,8,9-tetrahydro-10-methyl-8,8-bis(2-propenyl)pyrido[1,2-a]indol-9-one (12.8 g, 45.8 mmol), in ethanol (350 mL) at 25° C. The reaction mixture was stirred at room temperature for 24 hours. The solvent was removed in vacuo to near-dryness, and the residue partitioned between water (300 mL) and ether (300 mL). The separated organic layer was washed with brine (100 mL), dried over $MgSO_4$, filtered and evaporated to afford 12.63 g (98%) of the title compound as a light amber oil.

NMR ($CDCl_3$) δ1.55 (s, 1H, OH), 1.69-1.83 (m, 1H, H—7), 1.85-2.55 (multiplet with singlet spike at 2.32, 7H, $CH_2$, and $CH_3$—10), 3.33-3.52 (m, 1H, H—7), 3.82 (triplet of doublets, $J_1$=10.9 Hz, $J_2$=10.9 Hz, $J_3$=6.2 Hz, 1H, H—6), 4.14-4.26 (m, 1H, H—6), 4.70 (s, 1H, H—9), 4.92-5.29 (m, 4H, —CH=$CH_2$), 5.73-6.14 (m, 2H, —CH=), 7.09-7.31 (m, 3H, Ar—H), 7.59 (d, J=7.8 Hz, 1H, H—1);

MS (Relative intensity, fragment) m/e 281 (100, $M^+$), 240 (29, M—$CH_2$—CH=$CH_2$).

Step (3) Preparation of 6,7,8,9-Tetrahydro-10-methyl-8,8-bis(2-propenyl)-9-(1-pyrrolidinyl)-pyrido[1,2-a]indole Hydrochloride A solution of 6,7,8,9-tetrahydro-10-methyl-8,8-bis(2-propenyl)pyrido[1,2-a]indole-9-ol (4.3 g, 15.3 mmol), in dry pyridine (100 mL) was treated with a solution of methanesulfonyl chloride (3.488 g, 30.6 mmol) in dry pyridine (5 mL) at 0° C. The reaction mixture was stirred at 0° C. for ½ hour, then at 35° C. for 2 hours. Distilled pyrrolidine (23.8 g, 334 mmol) was added, and the mixture stirred, under exclusion of moisture, at 25° C. overnight. The solvent was removed in vacuo, the residue taken in ether (100 mL), and extracted with 1% hydrochloric acid (3×50 mL). The combined aqueous layers were basified with saturated sodium bicarbonate, and extracted with ether (3×80 mL). The combined organic layers were dried over $MgSO_4$, filtered, and evaporated to afford 1.07 g (21%) of the title base. The monohydrochloride salt was prepared with ethanolic hydrochloric acid, and recrystallized as a white powder from acetonitrile/ether (9:1), m.p. 155.5°-156.5° C.

IR (KBr) 3420 (broad), 2920, 2580, 2480, 1640, 1460, 1410, 920, 910, 740 $cm^{-1}$.

UV (MeOH) $\lambda_{max}$ 278.5 nm/ε=8217.

NMR (DMSO-$d_6$) δ2.31 (s, 3H, $CH_3$—10), 4.38 (dd, J=7.8 Hz, J=13.3 Hz, 1H, H—6 eq), 4.72 (s, 1H, H—9), 5.82 and 6.04 (multiplets, 1H+1H, —CH=), 7.13 (t, J=7.8 Hz, 1H, H—2), 7.26 (t, J=7.8 Hz, 1H, H—3), 7.45 (d, J=7.8 Hz, 1H, H—4), 7.6 (d, J=7.8 Hz, 1H, H—1);

MS (relative intensity, fragment) m/e 334 (13, $M^+$), 293 [15, M—($CH_2$—CH=$CH_2$)], 264 (49, M—pyrroline—$H^+$), 223 [100, 264—($CH_2$—CH=$CH_2$)];

Anal. Calcd.: C, 74.47; H, 8.42; N, 7.55%. Found: C, 74.46; H, 8.36; N, 7.52%.

EXAMPLE 11

6,7,8,9-Tetrahydro-8,8,10-trimethyl-9-(1-piperidinyl)-pyrido[1,2-a]indole (I: R=H, $R^1$ and $R^2$ =

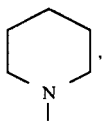

$R^3$ and $R^4$=—$CH_3$)

A soluion of 6,7,8,9-tetrahydro-8,8,10-trimethylpyrido[1,2-a]indol-9-ol (458 mg, 2 mmol, described in Example 1, Step 4), in dry pyridine (10 mL) was treated with methanesulfonyl chloride (458 mg, 4 mmol) at 0°–5° C. under exclusion of moisture. The reaction mixture was stirred at 40° C. for ½ hour then cooled to 0° C. Distilled piperidine (1.02 g, 12 mmol) was added at once. The mixture was stirred at 40°–50° C. for 4 hours, evaporated to dryness in vacuo, and the residue partitioned between ether (40 mL) and 5% sodium carbonate (40 mL). The separated organic layer was washed with 2% hydrochloric acid (3×20 mL) then basified to pH9 with saturated sodium carbonate. The product was extracted with toluene (4×25 mL). The combined organic layer was dried over MgSO4, filtered and evaporated in vacuo. The residue was crystallized as white needles from acetonitrile to afford 520 mg (88%) of the title base, m.p. 113°–115° C.

IR (KBr) 2985, 2930, 1460, 1355, 1340 cm$^{-1}$;

UV (MeOH) $\lambda_{max}$ 288, 295 nm/$\epsilon$ = 7990, 7840 respectively;

NMR (CDCl3) $\delta$0.81 (s, 3H, $CH_3$—8), 1.24 (s, 3H, $CH_3$—8), 1.26-1.62 (m, 7H, $CH_2$ and H—7), 2.24-2.46 (multiplets with a singlet spike at 2.28, 8H, H—7, $CH_2$—N—$CH_2$, $CH_3$—10), 3.43 (d, J=1.8 Hz, 1H, H—9), 3.82 (td, J=12 Hz, J=12 Hz, J=6 Hz, 1H, H—6), 4.1 (dd, J=12 Hz, J=8 Hz, 1H, H—6), 7.14-7.34 (m, 3H, Ar—H), 7.6 (d, J=8 Hz, 1H, H—1);

MS (relative intensity, fragment) m/e 296 (10, M+), 212 (100);

Anal. Calcd.: C, 81.03%; H, 9.52%; N, 9.45%. Found: C, 80.99%; H, 9.52%; N, 9.46%.

EXAMPLE 12

6,7,8,9-Tetrahydro-8,8,10-trimethyl-9-(1-morpholinyl)-pyrido[1,2-a]indole (I: R=—H, $R^1$ and $R^2$=

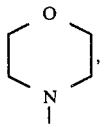

$R^3$ and $R^4$=—$CH_3$)

A solution of 6,7,8,9-tetrahydro-8,8,10-trimethylpyrido[1,2-a]indol-9-ol (2.44 g, 10.66 mmol, described in Example 1, Step 4), in anhydrous pyridine (50 mL) was treated with a solution of methanesulfonyl chloride (2.44 g, 21.32 mmol) in the same solvent (5 mL) at 0° C. The reaction mixture was stirred at 25° C. for 3 hours, cooled to 0° C. and treated slowly with a solution of morpholine (5.56 g, 64 mmol) in anhydrous pyridine (5 mL). After stirring at 0° C. for 1 hour, the mixture was left at 25° C. overnight, evaporated to near-dryness in vacuo and partitioned between ether (50 mL) and 5% sodium bicarbonate (3×20 mL). The separated organic layer was dried over MgSO4, filtered, and evaporated to dryness in vacuo. The residue was crystallized from acetonitrile to afford 1.38 g (43%) of the title base, m.p. 135.5°–137° C.

IR (KBr) 3050, 2970, 2940, 2880, 1465, 1330, 1120, 1000, 735 cm$^{-1}$;

UV (MeOH) $\lambda_{max}$ 231.5, 288, 294 nm/$\epsilon$=29,800, 7,500, 7,322;

NMR (CDCl3) $\delta$0.78 (s, 3H, $CH_3$—8), 1.21 (s, 3H, $CH_3$—8), 2.28 (s, 3H, $CH_3$—10), 3.39 (s, 1H, H—9), 3.53-3.67 (m, 4H, $CH_2$—N—$CH_2$), 3.76 (td, $J_1$=11.7 Hz, $J_2$=11.7 Hz, $J_3$=6.2 Hz, 1H, H—6), 4.17 (dd, $J_1$=11.7 Hz, $J_2$=7.8 Hz, 1H, H—6), 7.07-7.29 (m, 3H, Ar—H), 7.56 (d, 1H, H—1);

MS (relative intensity, fragment) m/e 298 (9.7, M+), 212 (100);

Anal. Calcd.: C, 76.47; H, 8.78; N, 9.39% Found: C, 76.23; H, 8.48; N, 9.35%.

EXAMPLE 13

6,7,8,9-Tetrahydro-8,8,10-trimethyl-N-(2-propynyl)-pyrido[1,2-a]indol-9-amine (I: R and $R^1$=—H, $R^2$=—$CH_2$—C≡CH, $R^3$ and $R^4$=$CH_3$)

A solution of 6,7,8,9-tetrahydro-8,8,10-trimethylpyrido[1,2-a]indol-9-ol (458 mg, 2 mmol, described in Example 1, Step (4) in dry methylene chloride (50 mL) was treated with thionylchloride (259 mg, 2.2 mmol). The reaction mixture was refluxed for 1½ hours, evaporated to dryness, and the residue partitioned between saturated NaHCO3 (20 mL) and chloroform (30 mL). The separated organic phase was dried over MgSO4, filtered, and evaporated in high vacuo. The obtained chloride was dissolved in dry tetrahydrofuran and treated with a solution of propargylamine (220 mg, 4 mmol) in the same solvent (5 mL) at 0° C. under exlusion of moisture. After 1 hour the reaction mixture was evaporated and the residue partitioned between 5% hydrochloric acid (20 mL) and toluene/ether (1:1, 30 mL). The separated aqueous phase was basified with K2CO3 powder and the product extracted with chloroform (40 mL). The separated organic phase was dried over MgSO4, filtered, and evaporated to afford 304 mg (58%) of the title base. The corresponding hydrochloride salt was prepared in ethanol with ethanolic HCl, and recrystallized from isopropanol/ether, m.p. 154°–5° C.

NMR (CDCl3) $\delta$0.81 (s, 3H, $CH_3$—8), 1.21 (s, 3H, $CH_3$—8), 1.49 (s, 1H, NH), 2.09-2.49 (multiplet with singlet spike at 2.38, 6H, $CH_2$—7, ≡CH, $CH_3$), 3.37 (d, J=2.4 Hz, 2H, NH—$CH_2$), 3.68-4.39 (m, 3H, $CH_2$—6 and H—9), 7.08-7.75 (m, 4H, Ar—H);

MS (relative intensity, fragment) m/e 266 (22, M+), 212 (59. loss of N+H2=CH—C≡CH), 198 (50, rearrangement, loss of $CH_3$—N+H=CH—C≡CH), 183 (13, 198—$CH_3$);

Anal. Calcd.: C, 71.38%; H, 7.65%; N, 9.25% Found: C, 71.20%; H, 7.57%; N, 9.20%.

EXAMPLE 14

6,7,8,9-Tetrahydro-N,10-dimethyl-N-(1-methylethyl)-pyrido[1,2-a]indol-9-amine (I: R, $R^3$ and $R^4$=—H, $R^2$=—$CH_3$, $R^4$=—CH($CH_3$)2

To a solution of 6,7,8,9-tetrahydro-10-methylpyrido[1,2-a]indole-9-ol (2.01 g, 10 mmol, described in Example 2, Step 1) in dry pyridine (150 mL) was added a solution of p-toluenesulfonyl chloride (7.6 g, 40 mmol)

in the same solvent (50 mL) at 0° C. Maintaining this temperature, stirring was continued for 60 minutes, and an excess of methylisopropylamine was added. The reaction mixture was stirred at ambient temperature for 3 hours, poured into water, and extracted with methylene chloride. The combined extracts were evaporated, and the residue was chromatographed. Elution with methylene chloride/methanol 20:1 afforded the title base.

NMR (CDCl$_3$) δ1.07 (d, J=7.5 Hz, 6H, CH$_3$ of isopropyl), 2.05 and 2.30 (singlets, 3H+3H, CH$_3$—N and CH$_3$), 2.98 (heptuplet, J=7.5 Hz, 1H, CH—N), 3.85-4.30 (multiplets, 3H, CH$_2$—6 and H—9).

EXAMPLE 15

6,7,8,9-Tetrahydro-2-methoxy-8,8,10-trimethyl-9-(1-pyrrolidinyl)-pyrido[1,2-a]indole Hydrochloride (I: R=2—OCH$_3$, R$^1$ and R$^2$=

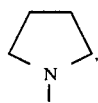

R$^3$ and R$^4$=—CH$_3$)

Step (1) Preparation of 4-(5-Methoxy-3-methyl-1H-indol-1-yl)butanoic acid (IV: R=5—OCH$_3$)

Anhydrous potassium carbonate (62 g, 0.45 mol) was added to a solution of 5-methoxy-3-methylindole (29 g, 0.18 mol, prepared according to E. Young (formylation) and R. Heacock (reduction), J. Chem. Soc., 1958, 3493 and Can. J. Chem., 42, 514, (1964) respectively) and γ-butyrolactone (77.5 g, 0.9 mol) in dimethylacetamide (1100 mL). Under mechanical stirring and protected with a drying tube, the reaction mixture was refluxed for 18 hours. More γ-butyrolactone (39 g, 0.45 mol) was added, and the reflux was continued for 12 hours. A final portion of γ-butyrolactone (19 g, 0.22 mol) was added and the thick suspension was refluxed for another 12 hours, cooled to ~30° C., and poured into water (1000 mL). Toluene (1000 mL) was added and the 2 phase system was vigorously stirred for 15 minutes. The aqueous layer was separated and acidified to pH2 with concentrated hydrochloric acid. The product was extracted with toluene (3×400 mL). The combined extracts were washed with water (1000 mL), dried over MgSO$_4$, filtered, and evaporated to afford the title product 36.1 g (82%) m.p. 69°-71° C. This acid was used in the next step without further purification.

NMR (DMSO-d$_6$) δ2.24 (s, 3H, CH$_3$), 1.6-2.4 (m, 4H, CH$_2$CH$_2$—CO), 3.78 (s, 3H, CH$_3$O), 4.1 (obscured triplet, J=6.5 H, 2H, CH$_2$—N), 6.79 (dd, Jo=9 Hz, Jm=2 Hz, 1H, H—6), 6.98 (br s, 1H, H—2), 7.01 (s, 1H, H—4), 7.38 (d, Jo=9 Hz, 1H, H—7);

MS (Relative intensity, fragment) m/e 247 (46, M+), 232 (5, M—CH$_3$), 174 (100, loss of CH$_2$CH$_2$COOH), 160 (8, 232-acrylic acid).

Step (2) Preparation of 6,7,8,9-Tetrahydro-2-methoxy-10-methylpyrido[1,2-a]indol-9-one (V: R=2—OCH$_3$)

4-(5-Methoxy-3-methyl-1H-indol-1-yl)butanoic acid (33 g, 0.133 mol) was heated in polyphosphoric acid (260 g) at 90° C. for 90 minutes. The dark reaction mixture was cooled to ~70° C. and poured into ice water (800 mL). The resulting suspension was stirred at 25° C. for 4 hours, the product was extracted with ether (4×400 mL), and the combined organic extracts were washed with saturated NaHCO$_3$ solution. The organic layer was separated, dried over MgSO$_4$, filtered, and evaporated to afford the title ketone 30 g, (98%). Analytical specimen was crystallized from ether to give a yellow solid, m.p. 145°-146° C.

NMR (CDCl$_3$) δ2.32 (m, 2H, CH$_2$—CO), 2.56 (obscured triplet, 2H, CH$_2$—CO), 2.65 (s, 3H, CH$_3$), 3.89 (s, 3H, OCH$_3$), 4.12 (t, J=5.5 Hz, 2H, N—CH$_2$), 6.95-7.35 (m, 3H, Ar—H);

MS (relative intensity, fragment) m/e 229 (100, M+), 228 (21, M—1), 214 (59, M—CH$_3$), 200 (21, loss of ethyl or CHO, alternatively 228—CO or ethylene), 186 (28, 214-ethylene or CO);

Anal. Calcd.: C, 73.34%; H, 6.59%; N, 6.11% Found: C, 73.47%; H, 6.68%; N 5.85%.

Step (3) Preparation of 6,7,8,9-Tetrahydro-2-methoxy-8,8,10-trimethylpyrido[1,2-a]indol-9-one (VI: R=2—OCH$_3$, R$^3$ and R$^4$=—CH$_3$)

To a solution of 6,7,8,9-tetrahydro-2-methoxy-10-methylpyrido[1,2-a]indol-9-one (2.29 g, 10 mmol) in t-butanol (150 mL) was added methyl iodide (17 g, excess), followed by a warm solution of potassium t-butoxide (4.5 g, 40 mmol) in t-butanol (60 mL). The reaction mixture was stirred at ambient temperature overnight, concentrated in vacuo, and the residue was partitioned between water and CH$_2$Cl$_2$. The organic layer was separated, washed with brine, dried (MgSO$_4$), filtered, and evaporated. The crude product was chromatographed on silica gel. Elution with chloroform-hexane 4:1 afforded 1.05 g (41%) of the title compound which solidified upon standing, m.p. 114°-115° C.

NMR (CDCl$_3$) δ1.28 (s, 6H, CH$_3$—8), 2.19 (t, J=7 Hz, 2H, CH$_2$—7), 2.62 (s, 3H, CH$_3$—10), 3.87 (s, 3H, CH$_3$O), 4.19 (t, J=7 Hz, 2 H, CH$_2$—6), 7.04 (s, 1H, H—1), 7.06 (d, J=8.6 Hz, 1H, H—3), 7.22 (d, J=8.6 Hz, 1H, H—4);

MS (relative intensity, fragment) m/e 257 (100, M+), 242 (79, M—CH$_3$).

Step (4) Preparation of 6,7,8,9-Tetrahydro-2-methoxy-8,8,10-trimethylpyrido[1,2-a]indol-9-ol (VII: R=2—OCH$_3$, R$^3$ and R$^4$=—CH$_3$)

To a solution of 6,7,8,9-tetrahydro-2-methoxy-8,8,10-trimethylpyrido[1,2-a]indol-9-one (1.07 g, 4.16 mmol) in methanol (100 mL) was added sodium borohydride (473 mg, 12.5 mmol), and the mixture was stirred overnight. The solvent was removed under reduced pressure, and the residue was partitioned between water and ether. The separated organic layer was washed with water, dried (MgSO$_4$), filtered, and evaporated. The product was crystallized from ether-hexane, m.p. 103°-104.5° C.; yield 850 mg (79%).

NMR (CDCl$_3$) δ0.9 and 1.19 (singlets, 6H, CH$_3$—8), 1.52-1.68 (multiplet with a singlet spike at 1.57, 2H, H—7 and exchangeable OH), 2.23-2.41 (multiplet with a singlet spike at 2.32, 4H, H—7 and CH$_3$—10), 3.87 (s, 3H, CH$_3$O), 3.83 and 4.15 (multiplets, 1H+1H, CH$_2$—6), 6.88 (dd, J$_o$=8.6 Hz, J$_m$=2 Hz, 1H, H—3), 6.99 (d, J$_m$=2 Hz, 1H, H—1), 7.17 (d, J$_o$=8.6 Hz, 1H, H—4).

MS (relative intensity, fragment) m/e 259 (88, M+), 242 (19, M—OH), 203 (100, loss of isobutylene).

Step (5) Preparation of 6,7,8,9-Tetrahydro-2-methoxy-8,8,10-trimethyl-9-(1-pyrrolidinyl)-pyrido[1,2]indole (I: R=2—OCH$_3$, R$^1$ and R$^2$=

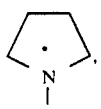

$R^3$ and $R^4$ =—CH$_3$)

A solution of 6,7,8,9-tetrahydro-2-methoxy-8,8,10-trimethylpyrido[1,2-a]indol-9-ol (777 mg, 3 mmol) in anhydrous pyridine (10 mL) was treated with methanesulfonyl chloride (687 mg, 6 mmol) at 25° C. The mixture was stirred for 2 hours, cooled to 0° C., and distilled pyrrolidine (1.28 g, 18 mmol) was added. Stirring was continued at room temperature overnight. The volatiles were removed in vacuo, the residue was mixed with 5% aqueous sodium bicarbonate, and extracted with ether. The combined extracts were dried (MgSO$_4$), filtered, and evaporated to give 932 mg of the title base.

The corrsponding hydrochloride was crystallized from acetonitrile-ether, m.p. 168°-170° C.

NMR (DMSO-d$_6$) δ0.77 and 1.43 (singlets, 3H+3H, CH$_3$—8), 2.30 (s, 3H, CH$_3$—10), 2.55 and 3.09 (multiplets, 1H+1H, CH$_2$—N), 3.4 and 3.8 (multiplets, 1H+1H, CH$_2$—N), 3.78 (s, 3H, CH$_3$O), 3.58 (td, J$_1$=12 Hz, J$_2$=6 Hz), 4.32 (dd, J$_1$=12 Hz, J$_2$=7 Hz), 4.76 (d, J=5 Hz, 1H, H—9), 6.88 (dd, J$_o$=8.6 Hz, J$_m$=2 Hz, 1H, H—3), 7.07 (d, J$_m$=2 Hz, 1H, H—1), 7.37 (d, J$_o$=8.6 Hz, 1H, H—4), 9.64 (br, 1H, NH$^+$);

MS m/e 312 (17), 242 (100).

Anal. Calcd.: C, 68.85%; H, 8.38%; N, 8.03% Found: C, 69.04%; H, 8.12%; N, 8.23%.

EXAMPLE 16

8,8-Diethyl-6,7,8,9-tetrahydro-2-methoxy-10-methyl-9-(1-pyrrolidinyl)pyrido[1,2-a]indole Hydrochloride (I: R=2—OCH$_3$, R$^1$ and R$^2$=

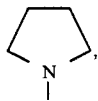

R$^3$ and R$^4$ =—CH$_2$—CH$_3$)

Step (1) Preparation of 8,8-Diethyl-6,7,8,9-tetrahydro-2-methoxy-10-methylpyrido[1,2-a]indol-9-one Sodium hydride (1.92 g, 48 mmol, ~60% in mineral oil) was added portionwise to a solution of 6,7,8,9-tetrahydro-2-methoxy-10-methylpyrido[1,2-a]indol-9-one (5 g, 21.8 mmol, described in Example 15, Step 2) in dimethylformamide (65 mL) under exclusion of moisture. The reaction mixture was stirred at 40° C. for 1 hour. Ethyl iodide (7.49 g, 48 mmol) was added dropwise over 10 minutes after stirring at 60° C. for 2 hours, the mixture was evaporated in vacuo to near-dryness and the residue suspended in water (60 mL). The organic products were extracted with ether (4×50 mL). The combined organic layers were washed with brine (100 mL), then dried over MgSO$_4$, filtered, and evaporated to dryness. The dark oily residue was chromatographed on silica gel (240 g). Flash elution with hexane/chloroform (6.5:3.5) afforded 510 mg of the title compound as an amber oil.

NMR (CDCl$_3$) δ0.90 (t, J=7.2 Hz, 6H, CH$_3$ of ethyl), 1.56-1.86 (m, 4H, CH$_2$ of ethyl), 2.24 (t, J=6 Hz, 2H, CH$_2$—7), 2.64 (s, 3H, CH$_3$—10), 3.90 (s, 3H, CH$_3$—O), 4.22 (t, J=6 Hz, 2H, CH$_2$—6), 7.06-7.18 (m, 2H, H—1, H—3), 7.24 (s, 1H, H—4);

MS (relative intensity, fragment) m/e 285 (72, M$^+$), 256 (100, M-ethyl).

Step (2) Preparation of 8,8-Diethyl-6,7,8,9-tetrahydro-2-methoxy-10-methylpyrido[1,2-a]indol-9-ol Sodium borohydride (380 mg, 10 mmol) was added portionwise to a solution of 8,8-diethyl-6,7,8,9-tetrahydro-2-methoxy-10-methylpyrido[1,2-a]indol-9-one (710 mg, 2.5 mmol) in ethanol (50 mL). The reaction mixture was stirred at 25° C. overnight. The solvent was evaporated in vacuo and the residue partitioned between 1% ammonium hydroxide (30 mL) and chloroform (49 mL). The separated organic layer was dried over MgSO$_4$, filtered, and evaporated to afford 530 mg (74%) of the desired alcohol as a light amber oil.

NMR (CDCl$_3$) δ0.76 (t, J=8 Hz, 3H, CH$_3$ of ethyl), 0.92 (t, J=8 Hz, 3H, CH$_3$ of ethyl), 1.00-1.72 (m, 5H, OH, CH$_2$ of ethyl), 2.04-2.30 (multiplet with singlet spike at 2.30, 5H, H—7, CH$_3$—10), 3.60-3.79 (m, 1H, H—6), 3.86 (s, 3H, CH$_3$O), 4.04-4.23 (m, 1H, H—6), 4.65 (s, 1H, H—9), 6.86 (dd, J=8.8 Hz, J=2.4 Hz, 1H, H—3), 6.99 (d, J=2.4 Hz, 1H, H—1), 7.15 (d, J=8.8 Hz, 1H, H—4);

MS (relative intensity, fragment) m/e 287 (31, M$^+$).

Step (3) Preparation of 8,8,-Diethyl-6,7,8,9-tetrahydro-2-methoxy-10-methyl-9-(1-pyrrolidinyl)pyrido[1,2-a]indole Hydrochloride Methanesulfonyl chloride (424 mg, 3.7 mmol) was added to a solution of 8,8-diethyl-6,7,8,9-tetrahydro-2-methoxy-10-methylpyrido[1,2-a]indol-9-ol (530 mg, 1.85 mmol) in anhydrous pyridine (18 mL) at 0° C. The reaction mixture was stirred at 40° C. for 1 hour, cooled to 25° C., and treated with pyrrolidine (790 mg, 11.1 mmol). After stirring another hour at 40° C., the mixture was evaporated in vacuo and the residue slurried in 2% hydrochloric acid (15 mL) for 20 minutes, then washed with ether (3×15 mL). The separated aqueous layer was basified with saturated Na$_2$CO$_3$ solution, then extracted with toluene (3×20 mL). The combined organic layers were dried over MgSO$_4$, filtered, evaporated, and the residue crystallized from ethanol to afford 500 mg (79%) of the title base, m.p. 98°-101° C. The hydrochloride salt was prepared in chloroform with ethanolic HCLl and recrystallized from acetonitrile as white microcrystals, m.p. 139°-142° C.

NMR (DMSO-d$_6$) δ0.68 (t, J=6.4 Hz, 3H, CH$_3$ of ethyl), 0.84-1.04 (multiplet, 5H, CH$_2$ of ethyl, and CH$_3$ of ethyl), 1.63-1.98 (m, 6H, CH$_2$), 2.32 (s, 3H, CH$_3$—10), 3.11-3.46 (m, 4H, CH$_2$—N—CH$_2$), 3.50-3.68 (m, 1H, H—6), 3.78 (s, 3H, CH$_3$O), 4.24-4.38 (m, 1H, H—6), 4.75 (br s, 1H, H—9), 6.91 (dd, J=9.2 Hz, J=2 Hz, 1H, H—3), 7.4 (d, J=2 Hz, 1H, H—1), 7.37 (d, J=9.2 Hz, 1H, H—4);

MS (relative intensity, fragment) m/e 340 (13, M$^+$), 270 (100, loss of pyrroline-H$^+$), 241 (55, 270-ethyl);

Anal. Calcd.: C, 70.09%; H, 8.82%; N, 7.43% Found: C, 69.88%; H, 8.84%; N, 7.26%.

EXAMPLE 17

2-Bromo-6,7,8,9-tetrahydro-8,8,10-trimethyl-9-(1-pyrrolidinyl)pyrido[1,2-a]indole Hydrochloride (I: R=2—Br, R$^1$ and R$^2$=

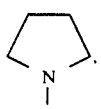

$R^3$ and $R^4$=—$CH_3$)

Step (1) Preparation of 2-Bromo-10-methyl-6,7,8,9-tetrahydropyrido[1,2-a]indol-9-one
(V: R=2—Br)

Aged N-bromosuccinimide (1 g) was added in small portions to a solution of 10-methyl-6,7,8,9-tetrahydropyrido[1,2-a]indol-9-one (described in Example 1, Step 2, 1.0 g), in methylene chloride (50 mL). The mixture was stirred at room temperature for 30 minutes, washed successively with water, 5% aqueous sodium bicarbonate, and water again. After drying (MgSO$_4$ and filtration), the solvent was evaporated, and the residue was crystallized from ether, m.p. 142°–144° C.; yield 1.25 g (90%).

NMR (CDCl$_3$) δ2.34 (m, 2H, CH$_2$), 2.57 (s, 3H, CH$_3$), 2.68 (m, 2H, CH$_2$—CO), 4.11 (t, J=5.5 Hz, 2H, CH$_2$N), 7.10 (d, $J_o$=8.5 Hz, 1H, H—4), 7.37 (dd, $J_o$=8.5 Hz, $J_m$=2 Hz, 1H, H—3), 7.75 (d, $J_m$=2 Hz, 1H, H—1).

Step (2) Preparation of 2-Bromo-6,7,8,9-tetrahydro-8,8,10-trimethylpyrido[1,2-a]indol-9-one
(VI: R=2—Br, $R^3$ and $R^4$=—$CH_3$)

To a refluxing solution of potassium t-butoxide (14.34 g, 128 mmol) in t-butanol (200 mL) was added at once a hot solution of 2-bromo-6,7,8,9-tetrahydro-10-methylpyrido[1,2-a]indol-9-one (8.89 g, 32 mmol) in the same solvent (100 mL). A solution of methyl iodide (54.5 g, 384 mmol) in t-butanol (100 mL) was then added dropwise. The reaction mixture was heated to reflux for 2 hours, evaporated in vacuo, and the residue was suspended in water (300 mL). The product was extracted with methylene chloride (3×100 mL), the combined extracts were washed with water, dried (MgSO$_4$), filtered, and concentrated. Chromatography on silica gel, eluting with hexane-methyene chloride 1:1, afforded 4.5 g (46%) of the title ketone, m.p. 112°–113° C. (methanol).

NMR (CDCl$_3$) δ1.28 (s, 6H, CH$_3$—8), 2.19 (t, J=7 Hz, 2H, CH$_2$—7), 2.61 (s, 3H, CH$_3$—10), 4.21 (t, J=7 Hz, 2H, CH$_2$—6), 7.18 (d, $J_o$=8.6 Hz, 1H, H—4), 7.42 (dd, $J_o$=8.6 Hz, $J_m$=1.8 Hz, 1H, H—3), 7.82 (very narrow doublet, 1H, H—1);

MS (relative intensity, fragment) m/e 307 (100, M+2), 305 (91, M+), 292 (63, loss of CH$_3$), 290 (63, loss of CH$_3$).

Step (3) Preparation of 2-Bromo-6,7,8,9-tetrahydro-8,8,10-trimethylpyrido[1,2-a]indol-9-ol
(VII: R=2—Br, $R^3$ and $R^4$=—$CH_3$)

Sodium borohydride (1.23 g, 32.6 mmol) was added portionwise to a solution of 2-bromo-6,7,8,9-tetrahydro-8,8,10-trimethylpyrido[1,2-a]indol-9-one (5 g, 16.3 mmol) in methanol (270 mL). The mixture was stirred at room temperature for 4 hours, evaporated, and the residue was partitioned between water and chloroform. Organic layer was dried (MgSO$_4$), filtered, and evaporated to give 4.95 g of the title alcohol, m.p. 135°–136° C.

NMR (CDCl$_3$) δ0.90 and 1.19 (singlets, 3H+3H, CH$_3$—8), 1.55–1.68 (m, 2H, H—7 and exchangeable OH), 2.2–2.4 (multiplet with a singlet spike at 2.29, 4H, H—7 and CH$_3$—10), 3.82 (td, $J_1$=$J_2$=12 Hz, $J_3$=5.5 Hz, 1H, H—6), 4.12 (m, 1H, H—6), 4.54 (br s, 1H, H—9), 7.12 (d, J=9 Hz, 1H, H—4), 7.28 (d, J=9 Hz, 1H, H—3), 7.68 (very narrow doublet 1H, H—1);

MS (relative intensity, fragment) m/e 309 (70, M+2), 307 (73, M+).

Step (4) Preparation of 2-Bromo-6,7,8,9-tetrahydro-8,8,10-trimethyl-9-(1-pyrrolidinyl)-pyrido[1,2-a]indole Hydrochloride
(I: R=2—Br, $R^1$ and $R^2$=

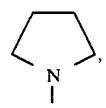

$R^3$ and $R^4$=—$CH_3$)

To a solution of 2-bromo-6,7,8,9-tetrahydro-8,8,10-trimethylpyrido[1,2-a]indol-9-ol (616 mg, 2 mmol) in anhydrous pyridine (10 mL) was added methanesulfonyl chloride (458 mg, 4 mmol) at room temperature. The reaction mixture was stirred for 60 minutes, cooled to 0° C., and distilled pyrrolidine (852 mg, 12 mmol) was added. Stirring was continued at room temperature for 2 hours, and then at 40° C. for 30 minutes. After adding a second portion of pyrrolidine (852 mg), the mixture was stirred at ambient temperature overnight, and then evaporated. The residue was partitioned between 5% aqueous NaHCO$_3$ and ether. The organic layer was washed with 1.5% hydrochloric acid, and the separated aqueous part was basified (pH 8) with a saturated solution of NaHCO$_3$. The product was extracted with ether, the combined extracts were dried (MgSO$_4$), filtered, and evaporated. The residual oil was chromatographed on neutral alumina (activity III). Elution with chloroform-hexane 1:1 afforded 355 mg (63%) of the title base. The corresponding hydrochloride salt was crystallized from ethanol-ether, m.p. 183.5°–184.5° C.

NMR (DMSO-d$_6$) δ0.80 and 1.49 (singlets, 3H+3H, CH$_3$—8), 2.32 (s, 3H, CH$_3$—10), 3.75 and 4.35 (multiplets, 1H+1H, CH$_2$—6), 4.80 (d, J=5 Hz, 1H, H—9), 7.42 (m, 2H, H—3 and H—4), 7.78 (very narrow doublet, 1H, H—1), 10.1 (br, 1H, NH+);

MS m/e 360 (15), 290 (100);

Anal. Calcd.: C, 57.37%; H, 6.59%; N, 7.04% Found: C, 57.33%, H, 6.54%; N, 6.93%.

EXAMPLE 18

2-Bromo-6,7,8,9-tetrahydro-N,N,10-trimethylpyrido[1,2-a]indol-9-amine Hydrochloride (I: R=2—Br, $R^1$ and $R^2$=—CH$_3$, $R^3$ and $R^4$=—H)
Step (1) Preparation of 2-Bromo-6,7,8,9-tetrahydro-10-methylpyrido[1,2-a]indol-9-ol To a solution of 2-bromo-10-methyl-6,7,8,9-tetrahydropyrido[1,2-a]indol-9-one (5.56 g, 20 mmol, described in Example 17, Step 1), in methanol (350 mL) was added sodium borohydride (2.5 g) portionwise, upon cooling. The reaction mixture was stirred at room temperature for 1 hour, and evaporated. The residue was partitioned between water and methylene chloride, the organic layer separated, dried (MgSO$_4$), filtered, and evaporated to obtain the title compound 3.4 g (61%), m.p. 120°–123° C.

NMR (CDCl$_3$) δ1.69 (d, J=4 Hz, 1H, OH, exchangeable), 1.6–2.3 (m, 4H, CH$_2$), 2.31 (s, 3H, CH$_3$), 3.70 (td, J=12 Hz, 4.5 Hz, 1H, H—6 ax), 4.15 (m, 1H, H—6 eq), 5.10 (m, t upon deuteration, J=3.5 Hz, 1H, H—9), 7.06

(d, J=8.5 Hz, 1H, H—4), 7.24 (dd, J=8.5 Hz, 1.8 Hz, 1H, H—3), 7.64 (d, J=1.8 Hz, 1H, H—1);

MS m/e (relative intensity, fragment) 281 (50, M+2), 279 (55, M+), 263 and 261 (100, loss of $H_2O$).

Step (2) Preparation of 2-Bromo-6,7,8,9-tetrahydro-N,N,10-trimethylpyrido[1,2-a]indol-9-amine hydrochloride To a solution of 2-bromo-6,7,8,9-tetrahydro-10-methylpyrido[1,2-a]indol-9-ol (2.8 g, 10 mmol), in dry pyridine (150 mL) was added a solution of p-toluenesulfonyl chloride (7.6 g, 40 mmol) in the same solvent (50 mL) at 0° C. Maintaining this temperature, stirring was continued for 60 minutes, and an excess of dimethylamine gas was indroduced from a lecture bottle. The reaction mixture was stirred at ambient temperature for 3 hours, poured into water, and extracted with methylene chloride. The combined extracts were evaporated, and the residue was chromatographed. Elution with methylene chloride/methanol 20:1 afforded the title base, 2.2 g (71%). The hydrochloride salt was crystallized from EtOH, m.p. 202°-203° C. as a beige solid.

IR (NUJOL) broad 2550 $cm^{-1}$;

UV (MeOH) $\lambda_{max}$ 284 nm ($\epsilon$=7,100), 233 nm ($\epsilon$=37,400);

NMR (DMSO-$d_6$) $\delta$2.30 (s, 3H, $CH_3$), 2.64 and 2.86 (doublets, J=3.5 Hz, 3H+3H, $CH_3$N), 4.78 (m, 1H, H—9), 7.2-7.5 (m, 2H, ArH), 7.74 (narrow doublet, 1H, H—1);

MS m/e (relative intensity, fragment) 308 and 306 (both 8, M+2 and M+), 264 and 262 (both 100, loss of $CH_3$—$N^+H$=$CH_2$), 263 and 261 (both 55, loss of dimethylamine);

Anal. Calcd.: C, 52.15%; H, 5.86%; N, 8.15% Found: C, 51.97%; H, 5.75%; N, 8.02%.

EXAMPLE 19

2-Bromo-6,7,8,9-tetrahydro-10-methyl-9-(1-piperidinyl)-pyrido[1,2-a]indole Hydrochloride (I: R=2—Br, $R^1$ and $R^2$=

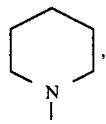

$R^3$ and $R^4$=—H)

To a solution of 2-bromo-6,7,8,9-tetrahydro-10-methylpyrido[1,2-a]indol-9-ol (2.8 g, 10 mmol, described in Example 18, Step 1), in dry pyridine (150 mL) was added a solution of p-toluenesulfonyl chloride (7.6 g, 40 mmol) in the same solvent (50 mL) at 0° C. Maintaining this temperature, stirring was continued for 60 minutes, and an excess of piperidine was introduced. The reaction mixture was stirred at ambient temperature for 3 hours, poured into water, and extracted with methylene chloride. The combined extracts were evaporated, and the residue was chromatographed. Elution with methylene chloride/methanol 20:1 afforded the title base. The hydrochloride salt was crystallized from EtOH, m.p. 225° C.

NMR (DMSO-$d_6$) $\delta$2.30 (s, 3H, $CH_3$), 4.76 (m, 1H, H—9), 7.15-7.45 (m, 2H, ArH), 7.75 (narrow doublet, 1H, H—1);

MS 348 and 346 (both 5, M+2 and M+), 263 and 261 (both 100, loss of piperidine);

Anal. Calcd.: C, 56.33%; H, 6.30%; N, 7.30% Found: C, 56.15%; H, 6.23%; N, 7.29%.

EXAMPLE 20

6,7,8,9-Tetrahydro-N,N,10-trimethylpyrido[1,2-a]indol-9-amine Hydrochloride (I: R, $R^3$, and $R^4$=—H, $R^2$ and $R^3$=—$CH_3$)

Step (1) Preparation of 6,7,8,9-Tetrahydro-10-methylpyrido[1,2-a]indol-9-one Oxime (IX: R, $R^3$ and $R^4$=—H)

The 10-methyl-6,7,8,9-tetrahydropyrido[1,2-a]indol-9-one (14.9 g, 74.8 mmol, described in Example 1, Step 2), was dissolved in pyridine (250 mL). Hydroxylamine hydrochloride (10.5 g, 151 mmol) was added and the resulting mixture refluxed for 90 minutes. The reaction mixture was concentrated in vacuo to ~80 mL volume, water (200 mL) was added, and the product was extracted with ether (3×150 mL). The combined organic extracts were washed with water (100 mL), 5% hydrochloric acid (100 mL), 10% aqueous sodium bicarbonate (150 mL), then dried over $MgSO_4$, filtered, and evaporated to afford 15 g (94%) of the title oxime. Analytical sample, recrystallized from ether-hexane, m.p. 160°-162° C.

IR ($CHCl_3$) 3260 $cm^{-1}$;

UV (MeOH) $\lambda_{max}$ 345 nm ($\epsilon$=4.290), 329 nm ($\epsilon$=8,700), 311 nm ($\epsilon$=17,935), and 242 nm ($\epsilon$=27,970);

NMR (DMSO-$d_6$) $\delta$2.08 (m, 2H, $CH_2$—7), 2.48 (s, 3H, $CH_3$), 2.85 (t, J=6.5 Hz, 2H, $CH_2$—8), 4.11 (t, J=5.5 Hz, 2H, $CH_2$—6), 7.0-7.75 (m, 4H, Ar—H), 11.2 (s, 1H, OH);

Anal. Calcd.: C, 72.87%; H, 6.59%; N, 13.08% Found: C, 73.15%; H, 6.87%; N, 13.04%.

Preparation of 6,7,8,9-tetrahydro-8,8,10-trimethylpyrido[1,2-a]indol-9-one oxime The title compound is prepared in an analogous manner to Step 1. A mixture of 6,7,8,9-tetrahydro-8,8,10-trimethylpyrido[1,2-a]indol-9-one (700 mg, 3.08 mmol, described in Example 1, Step 3), and hydroxylamine hydrochloride (420 mg, 6.04 mmol) was refluxed in pyridine (40 mL) for 2½ hours. The reaction mixture was evaporated to dryness in vacuo and the residue suspended in water (20 mL). The insoluble components were extracted with ether (3×40 mL). The combined organic layer was washed with 5% hydrochloric acid, 10% sodium bicarbonate, and water. The separated organic layer was dried over $MgSO_4$, filtered, and evaporated. The residue was chromatographed on silica gel (10 g). Elution with chloroform/hexane (1:1) afforded 300 mg (40%) of the title compound as a yellow oil.

NMR ($CDCl_3$) $\delta$1.30 (br s, 6H, $CH_3$), 2.08 (t, J=5.5 Hz, 2H, $CH_2$—7), 2.50 (s, 3H, $CH_3$) 4.05 (t, J=5.5 Hz, 2H, $CH_2$—6), 6.95-7.40 (m, 3H, ArH), 7.57 (m, 1H, H—1);

MS m/e (relative intensity, fragment) 242 (3, M+), 225 (7, M—OH), 197 (63, loss of $H_2O$ and HCN), 169 (100, 225-isobutylene).

Step (2) Preparation of 6,7,8,9-Tetrahydro-10-methylpyrido[1,2-a]indol-9-amine Hydrochloride (X: R, $R^3$ and $R^4$=—H).

Raney alloy (20 g) was added portionwise (over 40 minutes) to a solution of 6,7,8,9-tetrahydro-10-methylpyrido[1,2-a]indol-9-one oxime (13 g, 60.7 mmol) in ethanol (430 mL) and 10% aqueous sodium hydroxide (260 mL) at 35° C. The reaction mixture was stirred at 40°-45° C. for 12 hours, cooled to 25° C., and then poured into icy, saturated brine solution (500 mL). The product was extracted with ether (3×200 mL), and the combined extracts were washed with 5% hydrochloric acid. Upon cooling the separated aqueous layer was rendered basic with 50% aqueous sodium hydroxide, and extracted with ether (3×150 mL). The ethereal extracts were dried over MgSO$_4$, filtered, and evaporated to afford 11.7 g (97%) of the title amine which solidified, m.p. 52°-54° C.

MS m/e (relative intensity, fragment) 200 (60, M+), 183 (100, loss of NH$_3$).

The corresponding hydrochloride salt was crystallized from methanol-ether, m.p. 220°-223° C.

IR (NUJOL) 2,800 cm$^{-1}$;

UV (MeOH) $\lambda_{max}$ 285 nm ($\epsilon$=7,225), 277 nm ($\epsilon$=7,370);

NMR (DMSO-d$_6$) $\delta$2.05 (m, 4H, CH$_2$), 2.35 (s, 3H, CH$_3$), 3.95 and 4.25 (multiplets, 1H+1H, CH$_2$—6), 4.68 (m, 1H, H—9), 7.25 (m, 4H, ArH), 8.55 (br, 3H, N+H$_3$);

Anal. Calcd.: C, 65.89%; H, 7.23%; N, 11.90% Found: C, 65.56%; H, 7.04%; N, 11.78%.

Preparation of 2-Bromo-6,7,8,9-tetrahydro-10-methylpyrido[1,2-a]indol-9-amine

The title compound was prepared using the procedure described in Step 2, Method B. The product was purified by chromatography.

MS m/e (relative intensity, fragment) 280 and 278 (both 45, M+2 and M+), 263 and 261 (100 and 90, loss of NH$_3$);

NMR (CDCl$_3$) $\delta$1.56 (br s, 2H, NH$_2$), 1.8-2.5 (multiplets with a singlet spike at 2.25, 7H, CH$_2$ and CH$_3$), 3.35-4.45 (multiplets, 3H, CH$_2$—6 and H—9), 6.95-7.25 (m, 3H, ArH), 7.57 (d, J=1.8 Hz, 1H, H—1).

Step (3) Preparation of N-(6,7,8,9-Tetrahydro-10-methylpyrido[1,2-a]indol-9-yl)formamide A mixture of formic acid (b 6 mL) and acetic anhyride (12 mL) was heated at 60° C. for 4 hours. A solution of 6,7,8,9-tetrahydro-10-methylpyrido[1,2-a]indol-9-amine hydrochloride (7.5 g, 37.5 mmol), in dry tetrahydrofuran (60 mL) was added upon cooling to the resultant mixed anhydride. The reaction mixture was stirred at 25° C. for 2 hours, poured into water (150 mL) and extracted with ether (3×100 mL). The combined extracts were washed successively with 5% hydrochloric acid, 5% sodium bicarbonate, and water. The ethereal solution was dried over MgSO$_4$, filtered, and evaporated. The solid residue was crystallized from benzene/hexane to give 8.5 g (99%) of the title formamide as a yellow solid, m.p. 133°-5° C. Analytical sample melted at 136° C.

IR (NUJOL) 3420, 3300, and 1680 cm$^{-1}$;

NMR (CDCl$_3$) $\delta$2.05 (m, 4H, CH$_2$), 2.18 (s, 3H, CH$_3$), 3.8 and 4.2 (multiplets, 1H+1H, CH$_2$—6), 5.52 (m, 1H, H—9), 5.75 (br, 1H, NH), 6.95-7.30 (m, 3H, ArH), 7.52 (m, 1H, H—1), 8.08 (s, 1H, CHO);

MS m/e (relative intensity, fragment) 228 (58, M+), 213 (10, M—CH$_3$), 199 (20, M—CHO), 183 (100);

Anal. Calcd.: C, 73.65%; H, 7.06%; N, 12.27% Found: C, 73.70%; H, 7.15%; N, 12.17%.

Step (4) Preparation of 6,7,8,9-Tetrahydro-N,10-dimethylpyrido[1,2-a]indol-9-amine Hydrochloride N-(6,7,8,9-tetrahydro-10-methylpyrido[1,2-a]indol-9-yl)formamide (9.6 g) in 50 mL of dry benzene was added to a suspension of 3.4 g. of lithium aluminum hydride in 50 mL of dry benzene. The mixture was refluxed for 48 hours, and it was decomposed with tetrahydrofuran-water (1:1) solution. The inorganic portion was filtered off and the organic filtrate was dried and evaporated, giving 9.73 g of crude product. Chromatography on silica gel yielded 4.01 g (45%) of product. The basic material was converted to the hydrochloride and recrystallized from methanol-ether, m.p. 197°-198° C.

Anal. Calcd.: C, 67.05%; H, 7.63%; N, 11.16% Found: C, 67.00%; H, 7.68%; N, 11.00%.

IR (NUJOL) 2700 cm$^{-1}$;

UV (MeOH) $\lambda_{max}$ 285 and 277 nm; $\epsilon$=7,150 and 7,735 respectively;

NMR (DMSO-d$_6$) $\delta$ 2.32 (s, 3H, CH$_3$), 2.48 (s, 3H, CH$_3$—N), 4.62 (broad signal, 1H, H—9), 6.9-7.6 (m, 4H, ArH), 9.32 (br, 2H, N+H$_2$).

Step (5) Preparation of N-(6,7,8,9-Tetrahydro-10-methylpyrido[1,2-a]indol-9-yl)-N-methylformamide Formic acid (7 mL) and acetic anhydride (14 mL) were mixed and heated at 60° C. for 4 hours. A solution of 6,7,8,9-tetrahydro-N,10-dimethylpyrido[1,2-a]indol-9-amine hydrochloride (7.49 g, 35 mmol) in tetrahydrofuran (40 mL) was added, and the mixture was stirred at room temperature overnight. The resultant solution was poured onto ice, and products were extracted with ether. The combined extracts were washed with 5% hydrochloric acid, 5% bicarbonate, and water. After drying (MgSO$_4$) and filtration, the solvent was removed, and the residual oil was rapidly filtered through a silica gel column packed in chloroform/methanol 50:1. The title formamide was obtained as a yellowish oil 6.3 g (74%).

NMR (CDCl$_3$) indicates two rotamers: $\delta$2.1 (multiplet with spikes at 2.13 and 2.1, 7H, CH$_2$ and CH$_3$), 2.69 and 2.77 (singlets, 3H, CH$_3$—N), 4.02 (m, 2H, CH$_2$—6), 4.95 and 5.84 (broad signals, 1H, H—9), 69-7.35 (m, 3H, Ar—H), 7.52 (m, 1H, H—1), 8.14 and 8.17 (singlets, 1H, CHO).

Step (6) Preparation of N-(6,7,8,9-Tetrahydro-10-methylpyrido[1,2-a]indol-9-yl)-N-methylformamide A solution of N-(6,7,8,9-tetrahydro-10-methylpyrido[1,2-a]indol-9-yl)formamide (7.4 g, 32.4 mmol) in dimethylformamide (90 mL) was added dropwise at 25° C. to a suspension of sodium hydride (1.78 g, 37 mmol, ~50% suspension in mineral oil) in the same solvent (90 mL). The reaction mixture was stirred at 25° C. for 2 hours under exclusion of moisture. Methyl iodide (5.1 g, 35.6 mmol) was added and the mixture stirred at 25° C. overnight. The solvent was evaporated in vacuo and the residue partitioned between water (100 mL) and chloroform (150 mL). The organic layer was separated, dried over MgSO$_4$, filtered, and evaporated to afford 7.85 g (100%) of the title compound as an amber oil.

NMR (CDCl$_3$) indicates two rotamers: $\delta$2.1 (multiplet with spikes at 2.13 and 2.16, 7H, CH$_2$ and CH$_3$), 2.69 and 2.77 (singlets, 3H, CH$_3$—N), 4.02 (m, 2H, CH$_2$—6), 4.95 and 5.84 (broad signals, 1H, H—9), 6.9-7.35 (m, 3H, Ar—H), 7.52 (m, 1H, H—1), 8.14 and 8.17 (singlets, 1H, CHO);

MS m/e (relative intensity, fragment) 242 (60, M+), 213 (12, M—CHO), 199 (13, loss of CH$_3$ and CO), 183 (100, loss of CH$_3$—NH—CHO), * 138.4 for 242 to 183

Step (7) Preparation of 6,7,8,9-Tetrahydro-N,N,10-trimethylpyrido[1,2-a]indol-9-amine Hydrochloride A solution of N-(6,7,8,9-tetrahydro-10-methylpyrido[1,2-a]indole-9-yl)-N-methylformamide (9 g, 37.1 mmol) in tetrahydrofuran (50 mL) was added dropwise at 25° C. to a suspension of lithium aluminum hydride (1.6 g, 42.1 mmol) in the same solvent (50 mL). The reaction mixture was refluxed overnight under the exlusion of moisture. The metal complex was decomposed with a solution of water (3 mL) in tetrahydrofuran (20 mL) under nitrogen. The obtained suspension was filtered and the filtrate evaporated in vacuo. The residue was dissolved in CHCl$_3$ (100 mL), dried over MgSO$_4$, filtered, and evaporated in vacuo. The oily residue was chromatographed on silica gel (200 g). Elution with 2% MeOH in CHCl$_3$ afforded 6 g (71%) of the title base. The hydrochloride salt was prepared in CHCl$_3$ with excess etheral HCl, and recrystallized from methanol/ether as a white solid, m.p. 168°–9° C.

IR (CHCl$_3$) 2500 cm$^{-1}$;
UV (MeOH) $\lambda_{max}$ 276 nm ($\epsilon$=8,200);
NMR (CDCl$_3$) $\delta$2.05 (m, 4H, CH$_2$), 2.35 (s, 3H, CH$_3$), 2.57 and 2.94 (doublets, J=5.5 Hz, 6H, CH$_3$—N), 3.73 (td, J=11.5 Hz and 5 Hz, 1H, CH$_2$—6 ax), 4.32 (m, 1H, CH$_2$—6 eq), 4.53 (m, 1H, H—9), 7.25 (m, 3H, ArH), 7.52 (m, 1H, H—1), 11.23 (br, 1H, NH+);

MS m/e (relative intensity, fragment) 228 (30, M+), 184 (100, loss of CH$_2$=N+H—CH$_3$), 183 (95, loss of dimethylamine), 169 (40, 184—CH$_3$), 168 (35, 183—CH$_3$), * 146.88 for 228 to 183;

Anal. Calcd.: C, 68.03%; H, 7.99%; N, 10.58%
Found: C, 67.76%; H, 7.84%; N, 10.46%.

EXAMPLE 21

6,7,8,9-Tetrahydro-N,N,10-trimethylpyrido[1,2-a]indol-9-amine (I: R$^1$, R$^3$ and R$^4$=—H, R$^1$ and R$^2$=—CH$_3$)

The 6,7,8,9-tetrahydro-10-methylpyrido[1,2-a]indol-9-amine hydrochloride (600 mg, 3 mmol, described in Example 20, Step (2) and sodium bicarbonate powder (1.512 g, 18 mmol) were suspended in water (10 mL).. Dimethylsulfate (1.512 g, 12 mmol) was added at 10°–15° C. at once. The resulting suspension was heated to 50°–60° C. for 3½ hours, then stirred at 25° C. overnight. The product was extracted with CHCl$_3$ (3×30 mL). The combined extracts were dried over MgSO$_4$, filtered, and evaporated. The residue was chromatographed on silica gel (30 g). Elution with CHCl$_3$ afforded 400 mg (58%) of the title compound as a yellow oil.

NMR and MS of this product were identical with those described in Example 3.

EXAMPLE 22

6,7,8,9-Tetrahydro-N-(1-methylethyl)-10-methyl-pyrido[1,2-a]indol-9-amine (I: R, R$^1$=—H, R$^3$ and R$^4$=—H, R$^2$=—CH(CH$_3$)$_2$)

Molecular sieves (20 g, 4 Å type) were added to a solution of 6,7,8,9-tetrahydro-10-methylpyrido[1,2-a]indol-9-amine hydrochloride (8 g, 40 mmol, described in Example 20, Step 2) in acetone (200 mL). The reaction mixture was stirred at 25° C. for 14 hours. The sieves were removed by filtration and benzene (25 mL) was added to the filtrate. The mixture was evaporated and the residue dissolved in methanol (100 mL). Sodium borohydride (2 g, 52.6 mmol) was added portionwise and the reaction mixture stirred at 25° C. overnight. After evaporation of the mixture in vacuo, the residue was partitioned between water (60 mL) and ether (100 mL). The separated organic layer was dried over MgSO$_4$, filtered, and evaporated. The residue was chromatographed on silica gel (120 g). Elution with 2% methanol in chloroform afforded 6 g (62%) of the title base as a yellowish oil.

NMR (CDCl$_3$) $\delta$1.1 (d, J=6.5 Hz, 6H, CH$_3$ of isopropyl), 1.6–2.1 (m, 4H, CH$_2$), 2.30 (s, 3H, CH$_3$), 2.97 (heptuplet, J=6.5 Hz, 1H, CH of isopropyl), 3.69 (td, J=11.5 Hz and 5 Hz, 1H, CH$_2$—6 ax), 4.16 (m, 2H, CH$_2$—6 eq and H—9), 6.9–7.25 (m, 3H, ArH), 7.44 (m, 1H, H—1);

MS m/e (relative intensity, fragment) 242 (10, M+), 227 (3, M—CH$_3$), 199 (5, loss of isopropyl), 183 (100).

The corresponding hydrochloride salt was crystallized from ethanol-ether, m.p. 161°–162° C.

NMR (DMSO-d$_6$) $\delta$1.35 and 1.49 (doublets, J=7 Hz, 6H, CH$_3$ of isopropyl, 2.34 (s, 3H, CH$_3$), 4.84 (obscured triplet, 1H, H—9), 6.95–7.60 (m, 4H, ArH).

Anal. Calcd.: C, 68.92%; H, 8.31%; N, 10.04%
Found: C, 69.06%; H, 8.45%; N, 9.92%.

EXAMPLE 23

6,7,8,9-Tetrahydro-N,10-dimethyl-N-(1-methylethyl)-pyrido[1,2-a]indol-9-amine (I: R, R$^3$ and R$^4$=—H, R$^1$=—CH$_3$, R$^2$=—CH(CH$_3$)$_2$).

Step (1) Preparation of N-(6,7,8,9-Tetrahydro-10-methylpyrido[1,2-a]indol-9-yl)-N-(1-methylethyl)formamide A mixture of formic acid (6 mL) and acetic anhydride (12 mL) was heated at 60° C. for 4 hours. A solution of 6,7,8,9-tetrahydro-N-(1-methylethyl)-10-methyl-pyrido[1,2-a]indol-9-amine (6 g, 24.7 mmol, described in Example 22) in tetrahydrofuran (60 mL) was added at once at 25° C. under exclusion of moisture. The reaction mixture was stirred at 25° C. for 12 hours, then poured into ice water (120 mL). The product was extracted with ether (3×80 mL), and the combined organic layer washed with 5% HCl, 10% NaHCO$_3$, and water. The separated organic layer was dried over MgSO$_4$, filtered, and evaporated to afford 6 g (90%) of the title compound as an amber oil.

NMR (CDCl$_3$) clearly indicates the presence of two rotamers: $\delta$1.12 and 1.35, 1.37 and 1.43 (matching pairs of doublets, J=7 Hz, 6H, CH$_3$ of isopropyl), 2.08 (m, 4H, CH$_2$) 2.19 and 2.23 (singlets, 3H, CH$_3$), 3.21 and 3.84 (heptuplets, 1H, CH of isopropyl), 4.0 (m, 2H, CH$_2$—6), 4.86 and 5.94 (broadened triplets, 1H, H—9), 6.95–7.30 (m, 3H, ArH), 7.50 (m, 1H, H1), 7.88 and 8.39 (singlets, 1H, CHO);

MS m/e (relative intensity, fragment) 270 (100, M+), 277 (80, loss of C$_3$H$_7$), 199 (70, 227—CO), * 174.5 for 227 to 199

Step (2) Preparation of 6,7,8,9-Tetrahydro-N,10-dimethyl-N(1-methylethyl)pyrido[1,2-a]indol-9-amine A solution of N-(6,7,8,9-tetrahydro-10-methyl-pyrido[1,2-a]indol-9-yl)-N-(1-methylethyl)formamide (37.1 mmol) in tetrahydrofuran (50 mL) was added dropwise at 25° C. to a suspension of lithium aluminum hydride (1,6 g, 42.1 mmol) in the same solvent (50 mL). The reaction mixture was refluxed overnight under the exclusion of moisture. The metal complex was decomposed with a solution of water (3 mL) in the (20 mL) under nitrogen. The resulting suspension was filtered and the filtrate evaporated in vacuo. The residue was dissolved in CHCl$_3$ (100 mL), dried over MgSO$_4$, filtered, and evaporated in vacuo. The oily residue was chromatographed on silica gel (200 g). Elution with 2% MeOH in CHCl$_3$ afforded the title base.

NMR (CDCl₃) δ1.06 (d, J=7 Hz, 6H, CH₃ of isopropyl), 1.65-2.25 (m, 4H, CH₂), 2.05 and 2.30 (singlets, 6H, CH₃N and CH₃), 2.99 (heptinlet, 1H, CH of isopropyl), 3.75-4.30 (m, 3H, CH₂—6 and H—9);
MS m/e 256 (M+).

EXAMPLE 24

N-Ethyl-6,7,8,9-tetrahydro-10-methylpyrido[1,2-a]indol-9-amine Hydrochloride (I: R, R¹, R³ and R⁴=—H, R²=—C₂H₅)

Step (1) Preparation of N-(6,7,8,9-tetrahydro-10-methylpyrido[1,2-a]indole-9-yl)acetaminde A solution of 6,7,8,9-tetrahydro-10-methypyrido[1,2-a]indol-9-amine (2.0 g, described in Example 20, Step 2) in CH₂Cl₂ (20 mL) was added to 30% aqueous sodium hydroxide (12 mL), followed by dropwise addition of acetyl chloride (0.78 g). The mixture was stirred at room temperature for 2 hours, then diluted with water. The organic material was extracted with ether, washed with water and 10% solution of sodium bicarbonate. Evaporation of the solvent gave 2.3 g (100%) of crude product, which was recrystallized from benzene-hexane as a colorless solid, m.p. 158°-160° C.

IR (CHCl₃) 3430, 3300, 1663 cm⁻¹.

NMR (CDCl₃) δ2.01 (s, 3H, CH₃CO), 2.05 (m, 4H, CH₂), 2.27 (s, 3H, CH₃), 3.9-4.1 (m, 2H, CH₂—6), 5.4 (m, 1H, CH—9), 5.75 (br, 1H, NH), 7.25-7.55 (m, 4H, ArH);

Anal. Calcd.: C, 74.35; H, 7.49; N, 11.56% Found: C, 74.24; H, 7.44; N, 11.50%.

Step (2) Preparation of N-Ethyl-6,7,8,9-tetrahydro-10-methylpyrido[1,2-a]indol-9-amine Hydrochloride A solution of N-(6,7,8,9-tetrahydro-10-methylpyrido[1,2-a]indol-9-yl)acetamide 13.6 g dissolved in 100 mL of dry benzene was added dropwise to a suspension of 4.7 g of lithium aluminum hydride in 50 mL of dry benzene. The mixture was refluxed for 48 hours and then decomposed with 1:1 tetrahydrofuranwater solution. The inorganic portion was filtered off and the filtrate was dried and evaporated, giving 11.5 g of the crude product. Chromatography on silica gel (10% methanol in chloroform) yielded 6.0 g (51%) of the title base, which was converted to the hydrochloride, m.p. 184°-186° C. (methanol-ether).

IR (NUJOL) 2,750 cm⁻¹;

UV (MeOH) λ$_{max}$ 284 nm (ε=6,900); 277 nm (ε=7,275);

NMR (CDCl₃) δ1.36 (t, J=7 Hz, 3H, CH₃ of ethyl), 2.37 (s, 3H, CH₃), 4.55 (br s, 1H, H—9);

Anal. Calcd.: C, 68.03; H, 7.99; N, 10.57% Found: C, 67.97; H, 8.04; N, 10.56%.

EXAMPLE 25

6,7,8,9-Tetrahydro-2-methoxy-N,10-dimethyl-pyrido[1,2-a]indol-9-amine(Z)-2-butenenedioate (I: R=2—OCH₃, R¹, R³ and R⁴=—H, R²=—CH₃)

Step (1) Preparation of 6,7,8,9-Tetrahydro-2-methoxy-10 -methylpyrido[1,2-a]indol-9-one Oxime 6,7,8,9-Tetrahydro-2-methoxy-10-methylpyrido[1,2-a]indol-9-one, (9.16 g, 0.04 mol, described in Example 15, Step 2), was dissolved in pyridine (180 mL). Hydroxylamine hydrochloride (5.56 g, 0.08 mol) was added and the resulting solution refluxed for 90 minutes. The reaction mixture was concentrated in vacuo to ~15 mL, water (200 mL) was added and the product was extracted with ether (2×50 mL). The combined organic extracts were washed with water (100 mL), 5% hydrochloric acid (50 mL), 10% aqueous sodium bicarbonate (100 mL), then dried over MgSO₄, filtered, and evaporated to afford the desired oxime 9.2 g (94%) m.p. 174°-6° C.

NMR (DMSO—d₆) δ2.02 (m, 2H, CH—7), 2.48 (s, 3H, CH₃), 2.82 (t, J=6 Hz, 2H, CH₂—8), 3.8 (s, 3H, CH₃O), 4.08 (t, J=5.5 Hz, 2H, CH₂—6), 6.88 (dd, Jo=9 Hz, Jm=2.4 Hz, 1H, H—3), 7.10 (d, Jm=2.4 Hz, 1H, H—1), 7.38 (d, Jo=9 Hz, 1H, H—4), 11.3 (s, 1H, NOH);

MS (relative intensity, fragment) m/e 244 (64, M+), 227 (100, M—OH), 199 (36,227-ethylene).

Step (2) Preparation of 6,7,8,9-Tetrahydro-2-methoxy-10-methylpyrido[1,2-a]indol-9-amine Raney alloy (10.2 g) was added portionwise (over 40 minutes) to a solution of 6,7,8,9-tetrahydro-2-methoxy-10-methylpyrido[1,2-a]indol-9-one oxime (6.2 g, 25.4 mmol) in ethanol (200 mL) and 10% aqueous sodium hydroxide (100 mL) at ~35° C. The reaction mixture was stirred at 40° C. for 12 hours, cooled to 25° C., and then poured into icy, saturated brine solution (500 mL). The product was extracted with ether (2×200 mL), and the combined extracts were washed with 5% hydrochloric acid (200 mL). Upon cooling the separated aqueous layer was rendered basic with 50% aqueous sodium hydroxide, and extracted with ether (3×150 mL). The ethereal extracts were dried over MgSO₄, filtered, and evaporated to afford 5.8 g (99%) of the title amine as a yellow oil.

IR (CHCl₃) 3380, 3320, and 1615 cm⁻¹;

NMR (CDCl₃) δ1.82 (s, 2H, NH₂), 1.98 (m, 4H, CH₂), 2.35 (s, 3H, CH₃), 3.9 (2, 3H, CH₃O), 4.03 (m, 2H, CH₂—6), 4.40 (t, J=6.5 Hz, 1H, H—9), 6.75-7.35 (m, 3H, Ar—H);

MS (relative intensity, fragment) m/e 230 (48, M+), 229 (10, M—1), 215 (30, M—CH₃), 213 (100, M—NH₃), 198 (25, 215—NH₃).

Step (3) Preparation of N-(6,7,8,9-Tetrahydro-2-methoxy-10-methylpyrido[1,2-a]indol-B 9-yl)-formamide A mixture of formic acid (6 mL) and acetic anhydride (12 mL) was heated at 60° C. for 4 hours. A solution of 6,7,8,9-tetrahydro-2-methoxy-10-methylpyrido[1,2-a]indol-9-amine (5.8 g, 25.2 mmol) in dry tetrahydrofuran (60 mL) was added upon cooling to the resultant mixed anhydride. The reaction mixture was stirred at 25° C. overnight, poured into water (100 mL), and extracted with ether (3×70 mL). The combined extracts were washed successively with 5% hydrochloric acid (80 mL), 5% aqueous sodium bicarbonate (100 mL), and water (100 mL). The ethereal solution was dried over MgSO₄, filtered, and evaporated. The solid residue was crystallized from ether-hexane to give 5.4 g (83%) of the title formamide, m.p. 130°-132° C. as a beige solid.

NMR (CDCl₃) δ1.98 (broad signal, 4H, CH₂), 2.17 (s, 3H, CH₃), 3.6-4.3 (multiplets with a singlet spike at 3.82, 5H, CH₂—6 and CH₃O), 4.63-5.45 (multiplets, 1H, H—9), 6.22 (m, 1H, NH), 6.80-7.33 (m, 4H, Ar—H), 8.07 (br s, 1H, CHO);

MS (relative intensity, fragment) m/e 258 (55, M+), 243 (12, M—CH₃), 229 (19, M—CHO), 214 (50, 243—CHO or 229—CH₃), 213 (100, loss of formamide).

Step (4) Preparation of 6,7,8,9-Tetrahydro-2-methoxy-N,10-dimethylpyrido[1,2-a]indol-9-amine (Z)-2-butenenedioate A solution of N-(6,7,8,9-tetrahydro-2-methoxy-10 -methylpyrido[1,2-a]indol-9-yl)-formamide (4.2 g, 16.2 mmol) in dry tetrahydrofuran (80 mL) was added dropwise (over 20 minutes) to stirred suspension of lithium aluminum hydride (2.24 g, 32.6 mmol) in the same solvent (100 mL). The reaction mixture was refluxed for 12 hours, and then allowed to cool. The resulting complex salt was decomposed (under nitrogen and upon cooling) with wet tetrahydrofuran (1 mL of $H_2O$ in 10 mL of tetrahydrofuran), the slurry was stirred for 30 minutes, anhydrous $MgSO_4$ was added, and the mixture was filtered. The solvent was removed with rotavapor, and the title base solidified 3.95 g, (99%) m.p. 85°–88° C. A sample was converted to the maleate salt, m.p. 143°–145° C. (ethanol-ether).

IR (CHCl$_3$) 3400, 2740, 2470 (broad bands), 1710, 1625, 1575, and 1360 cm$^{-1}$;

UV (MeOH) $\lambda_{max}$ 306 nm ($\epsilon$4,970), 280 nm ($\epsilon$9,410);

NMR (CDCl$_3$) $\delta$2.2 (br m, 4H, CH$_2$), 2.35 (s, 3H, CH$_3$), 2.66 (s, 3H, CH$_3$—N), 3.87 (s, 3H, CH$_3$—O), 3.55 and 4.4–4.9 (multiplets, 1H+2H, CH—N and CH$_2$—N, 6.15 (s, 2H, =CH—CO), 6.89 (dd, Jo=8.5 Hz, Jm=2 Hz, 1H, H—3), 7.07 (narrow doublet, 1H, H—1, 7.29 (d, Jo=8.5 Hz, 1H, H—4);

MS (relative intensity, fragment) m/e 244 (20, M+), 229 (4, M—CH$_3$), 214 (57, 229—CH$_3$), 213 (100, loss of CH$_3$NH$_2$), 212 (19, 213—H), 198 (25, 229—CH$_3$NH$_2$).

Anal. Calcd.: C, 63.32%; H, 6.71%; N, 7.77% Found: C, 63.08%; H, 6.69%; N, 7.72%.

EXAMPLE 26

6,7,8,9-Tetrahydro-2-methoxy-N,N,10-trimethyl-pyrido[1,2-a]indol-9-amine Hydrochloride (I: R=2—OCH$_3$, R$^1$, R$^2$=—CH$_3$, R$^3$, R$^4$=—H)

Step (1) Preparation of N-(6,7,8,9-Tetrahydro-2-methoxy-10-methylpyrido[1,2-a]indol-9-yl)-N-methylformamide A mixture of formic acid (3.05 g, 66.3 mmol) and acetic anhydride (5.4 g, 55 mmol) was heated at 60° C. for 4 hours. A solution of 6,7,8,9-tetrahydro-2-methoxy-N,10-dimethylpyrido[1,2-a]indol-9-amine (2 g, 8.2 mmol, described in Example 27) in dry tetrahydrofuran (20 mL) was added upon cooling to the resultant mixed anhydride. The reaction mixture was stirred at 25° C. overnight, poured into water (40 mL), and extracted with ether (3×40 mL). The combined extracts were washed successively with 5% hydrochloric acid (50 mL), 5% aqueous sodium bicarbonate (60 mL), and water (80 mL). The ethereal solution was dried over MgSO$_4$, filtered, and evaporated to afford 2.1 g (95%) of the title formamide as a yellow oil.

NMR (CDCl$_3$) clearly indicates the presence of two rotamers: $\delta$1.7–2.5 (multiplets with singlet spikes as 2.16 and 2.24, 7H, CH$_2$, CH$_3$), 2.72 and 2.80 (singlets, 3H, CH$_3$—N), 3.6–4.15 (multiplets with a broad singlet at 3.87, 5H, CH$_2$—6 and CH$_3$—O), 4.95 and 5.88 (broad, 1H, H—9), 6.8–7.3 (m, 3H, Ar—H), 8.22 (br s, 1H, CHO);

MS (relative intensity, fragment) m/e 272 (55, M+), 257 (4, M—CH$_3$), 243 (13, M—CHO), 229 (20, 257—CO), 213 (100, loss of CH$_3$NH—CHO), 198 (32, 213—CH$_3$).

Step (2) Preparation of 6,7,8,9-Tetrahydro-2-methoxy-N,N,10-trimethylprido[1,2-a]indol-9-amine Hydrochloride A solution of N-(6,7,8,9-tetrahydro-2-methoxy-10-methylpyrido[1,2-a]indol-9-yl)-N-methylformamide (2.1 g, 7.7 mmol) in dry tetrahydrofuran (30 mL) was added dropwise over 12 minutes to a suspension of lithium aluminum hydride (304 mg, 8 mmol) in the same solvent (20 mL). The reaction mixture was stirred for 12 hours at room temperature, and then, a solution of water (0.9 g) in tetrahydrofuran (10 mL) was carefully added upon cooling and under nitrogen. The resulting precipitate was filtered off, the filtrate was dried (MgSO) filtered, and evaporated. The oily residue was chromatographed on neutral alumina (40 g, activity III). Elution with chloroform afforded the title base 1 g (50%). The hydrochloride salt was prepared in ethanol, and recrystallized from ethanol as a light beige solid, m.p. 163°–165° C.

IR (NUJOL) 2600, 2580, and 2480 cm$^{-1}$;

UV (MEOH) $\lambda_{max}$ 306, 280, and 221 nm, $\epsilon$=4870, 2920, and 21,580 respectively;

NMR (CDCl$_3$) $\delta$1.70–2.15 (m, 4H, CH$_2$), 2.31 (s, 3H, CH$_3$), 2.63 and 2.86 (two non-first-order signals, 3H+3H, CH$_3$—N), 3.78 (s, 3H, CH$_3$O), 3.95–5.0 (m, 3H, CH$_2$—6, H—9), 6.86 (dd, J$_o$=8.5 Hz, J$_m$=2 Hz, 1H, H—3), 7.05 (d, J$_m$=2 Hz, 1H, H—1), 7.05 (d, J$_m$=2 Hz, 1H, H—1), 7.40 (d, J$_o$=8.5 Hz, 1H, H—4);

MS (relative intensity, fragment) m/e 258 (6, M+), 214 (100, loss of CH$_3$—N+H=CH$_2$), 213 (56, loss of dimethylamine), 199 (16), 198 (15);

Anal. Calcd.: C, 65,18%; H, 7.86%; N, 9.50% Found: C, 64.89%; H, 7.69%; N, 9.22%.

EXAMPLE 27

6,7,8,9-Tetrahydro-3-methoxy-N,10-dimethyl-pyrido[1,2-a]indol-9-amine Hydrochloride (I: R=3—OCH$_3$, R$^1$, R$^3$ and R$^4$=—H, R$^2$=—CH$_3$)

Step (1) Preparation of 4-(6-methoxy-3-methyl-1H-indol-1-yl)butanoic Acid

Anhydrous potassium carbonate (34.5 g, 0.25 mol) was added to a solution of 6-methoxy-3-methylindole (16.1 g, 0.1 mol) and $\gamma$-butyrolactone (43 g, 0.5 mol) in dimethylacetamide (750 mL). Under mechanical stirring and protected with a drying tube, the reaction mixture was refluxed for 18 hours, more $\gamma$-butyrolactone (21.5 g, 0.25 mol) was added, and the reflux was continued for 12 hours. A final portion of $\gamma$-butyrolactone (21.5 g, 0.25 mol) was added and the thick suspension was refluxed for another 12 hours, cooled to ~30° C., and poured into water (600 mL). Toluene (600 mL) was added and the 2 layer system was stirred for 15 minutes. The aqueous layer was separted and acidified with concentrated hydrochloric acid. The product was extracted with toluene (3×250 mL). The combined extracts were washed with water (600 mL), dried over MgSO$_4$, filtered, evaporated, and the dark oily residue was chromatographed on silica gel (480 g). Elution with chloroform/hexane (1:1) afforded 18.2 g (74%) of the title compound as a yellowish oil.

NMR (CDCl$_3$) $\delta$2.3 (s, 3H, CH$_3$), 1.8–2.5 (m, 4H, CH$_2$—CH$_2$—CO), 3.9 (s, 3H, CH$_3$O), 3.9–4.4 (m, 2H, CH$_2$—N), 6.65–7.00 (multiplets with a singlet spike at 6.86, 3H, Ar—H), 7.42 (obscured doublet, 1H, H—4);

MS (relative intensity, fragment) m/e 247 (55, M+), 232 (8, M—CH$_3$), 174 (76, loss of CH$_2$—CH$_2$—COOH), 160 (13, 232-acrylic acid).

The starting 6-methoxy-3-methylindole was prepared according to T. Wieland and D. Grimm, Chem. Ber., Jahrgang 98, 1727. Diazotized m-anisidine was coupled with ethyl $\alpha$-ethylacetoacetate to afford the m-methoxyphenylhydrazon of the $\alpha$-keto-butyric acid ethylester (Japp-Klingemann method), which was subjected to the acid catalyzed cyclization (Fisher Indole Synthesis). Hydrolysis and decarboxylation led to the requisite starting material.

Step (2) Preparation of 6,7,8,9-Tetrahydro-3-methoxy-10-methylpyrido[1,2-a]indol-9-one 4-(6-Methoxy-3-methyl-1H-indol-1-yl)butanoic acid (24.7 g, 0.1 mol) was heated in polyphosphoric acid (250 g) at 90° C. for 90 minutes. The dark reaction mixture was cooled to ~70° C. and poured into ice water (800 mL). The resulting suspension was extracted with ether (4×400 mL), and the combined organic extracts were washed with saturated NaHCO$_3$ solution. The organic layer was separated, dried over MgSO$_4$, filtered, and evaporated to afford the title ketone 20 g (87%). An analytical specimen was recrystallized from MeOH-water, m.p. 131.5°–133.5° C. as a beige solid.

NMR (CDCl$_3$) δ2.25 (m, 4H, CH$_2$—CH$_2$—CO), 2.65 (s, 3H, CH$_3$), 3.90 (s, 3H, OCH$_3$), 4.09 (t, J=5.5 Hz, 2H, N—CH$_2$), 6.68 (d, Jm=3 Hz, 1H, H—4), 6.80 (dd, Jo=9 Hz, Jm=3 Hz, 1H, H—2), 7.57 (d, Jo=9 Hz, 1H, H—1);

MS (relative intensity, fragment) m/e 229 (100, M+), 228 (14, M—1), 214 (62, M—CH$_3$), 200 (9.5, loss of ethyl or CHO, alternatively 228—CO or ethylene), 186 (44, 214-ethylene or CO);

Anal. Calcd.: C, 73.34%; H, 6.59%; N, 6.11% Found: C, 73.53%; H, 6.52%; N, 5.79%.

Step (3) Preparation of 6,7,8,9-Tetrahydro-3-methoxy-10-methylpyrido[1,2-a]indol-9-one Oxime A solution of 6,7,8,9-tetrahydro-3-methoxy-10-methylpyrido[1,2-a]indol-9-one (2.29 g, 10 mmol) and hydroxylamine hydrochloride (1.39 g, 20 mmol) in dry pyridine (40 mL) was refluxed for 2 hours. The reaction mixture was concentrated to 10% of its original volume and distilled water (80 mL) was added. The organic product was extracted with ether (3×60 mL). The combined organic layers were washed with water (100 mL), 5% hydrochloric acid (50 mL), and 10% sodium bicarbonate (50 mL). The separated organic layer was dried over MgSO$_4$, filtered, and evaporated. The residue was recrystallized from methanol/water to afford 2.4 g (98%) of the title compound as gray microcrystals.

NMR (CDCl$_3$) δ2.08 (quint., J=6 Hz, 2H, CH$_2$—7), 2.5 (s, 3H, CH$_3$—10), 2.98 (t, J=6 Hz, 2H, CH$_2$—8), 3.88 (s, 3H, OCH$_3$), 4.0 (t, J=6 Hz, 2H, CH$_2$—6), 6.75 (s, 1H, H—4), 6.9 (dd, J$_o$=8 Hz, J$_m$=2 Hz, 1H, H—2), 7.55 (d, J$_o$=8 Hz, 1H, H—1), 9.48 (br s, 1H, NOH);

MS (relative intensity, fragment) m/e 244 (64, M+), 227 (100, M—OH).

Step (4) Preparation of 6,7,8,9-Tetrahydro-3-methoxy-10-methylpyrido[1,2-a]indol-9-amine A solution of 6,7,8,9-tetrahydro-3-methoxy-10-methylpyrido[1,2-a]indol-9-one oxime (2.2 g, 9 mmol) in ethanol (50 mL) containing 10% sodium hydroxide (36 mL) was treated with Raney alloy (3.15 g) at 35° C. over 20 minutes. The reaction mixture was stirred at 45° C. for 18 hours, then poured into ice water (100 mL), saturated with sodium chloride. The product was extracted with ether (3×75 mL), dried and evaporated. The residue was dissolved in toluene (30 mL), and extracted with 3% hydrochloric acid (50 mL). The aqueous layer was separated, and basified with 50% sodium hydroxide upon cooling. The product was extracted with chloroform, dried over MgSO$_4$, filtered, and evaporated. The dark oily residue was chromatographed on silica gel (50 g). Elution with chloroform afforded 1.87 g (91%) of the desired amine as an amber oil.

NMR (CDCl$_3$) δ1.65 (s, 2H, NH$_2$), 2.01 (m, 4H, CH$_2$), 2.35 (s, 3H, CH$_3$—10), 3.62-4.15 (multiplet with singlet spike at 3.91, 5H, CH$_2$—6, CH$_3$O), 4.42 (t, 1H, H—9), 6.71-6.98 (m, 2H, H—2, H—4), 7.58 (d, 1H, H—1);

MS (relative intensity, fragment) m/e 230 (59, M+), 229 (11, M—1H), 214 (100, 229—CH$_3$), 213 (63, loss of NH$_3$), 199 (23, 214—CH$_3$).

Step (5) Preparation of N-(6,7,8,9-Tetrahydro-3-methoxy-10-methylpyrido[1,2-a]indol-9-yl)formamide A mixture of formic acid (8.5 g,) and acetic anhydride (15.2 g) was heated to 60° C. for 4 hours, then cooled to 0° C. A solution of 6,7,8,9-tetrahydro-3-methoxy-10-methylpyrido[1,2-a]indol-9-amine (6.1 g, 26.6 mmol) in tetrahydrofuran (50 mL) was added at 0° C. The reaction mixture was stirred at 0° C. for 3 hours under exclusion of moisture. It was then poured into water (75 mL) and extracted with ether (3×100 mL). The combined organic layers were washed with 5% hydrochloric acid (50 mL), and then with saturated sodium bicarbonate (3×50 mL). The separated organic layer was dried over MgSO$_4$, filtered, and evaporated to afford 5.25 g (77%) of the title compound as an off white solid, m.p. 181°–182.5° C.

NMR (CDCl$_3$) δ1.89–2.32 (multiplet with singlet spike at 2.18, 7H, CH$_2$ and CH$_3$—10), 3.59–4.24 (multiplet with singlet spike at 3.82, 6H, CH$_2$—6, H—9, CH$_3$O), 5.32–5.62 (m, 1H, NH), 6.6–7.3 (m, 3H, Ar—H), 8.13 (br s, 1H, CHO);

MS (relative intensity, fragment) m/e 258 (99, M+), 243 (37, M—CH$_3$), 229 (14, M—CHO), 214 (100, 299—CH$_3$).

Step (6) Preparation of 6,7,8,9-Tetrahydro-3-methoxy-N,10-dimethylpyrido[1,2-a]indol-9-amine Hydrochloride A solution of N-(6,7,8,9-tetrahydro-3-methoxy-10-methylpyrido[1,2-a]indol-9-yl)formamide (4 g, 15.5 mmol) in dry tetrahydrofuran (75 mL) was added to a suspension of lithium aluminum hydride (1.2 g, 31 mmol) in the same solvent (40 mL) over 45 minutes. The reaction mixture was refluxed for 18 hours under exclusion of moisture. The metal complex was decomposed at 0° C. under nitrogen by addition of 5% aqueous tetrahydrofuran (10 mL) in a dropwise fashion. After 30 minutes, stirring at 25° C., the mixture was dried over MgSO$_4$, filtered, and evaporated to afford 3.4 g (90%) of the title base. The hydrochloride salt was prepared in ethanol with ethereal HCl and recrystallized from ethanol/ether as an off whie solid, m.p. 175° C.

IR (NUJOL) 3430 (broad), 1630 cm$^{-1}$;

UV (MeOH) λ$_{max}$ 299 nm (ε=7,880);

NMR (DMSO—d$_6$) δ1.8–2.7 (multiplets with singlet spikes at 2.28 and 2.46, 10H, CH$_2$—7, CH$_2$—8, CH$_3$), 3.73 (s, 3H, CH$_3$O), 4.62 (narrow multiplet, 1H, H—9), 6.51–6.97 (m, 2H, ArH), 7.41 (d, J=9 Hz, 1H, H—1);

MS m/e (relative intensity, fragment) 244 (36, M+), 214 (100);

Anal. Calcd.: C, 64.16%, H, 7.54%; N, 9.98% Found: C, 63.84%; H, 7.30%; N, 9.81%

EXAMPLE 28

6,7,8,9-Tetrahydro-3-methoxy-N,N,10-trimethyl-pyrido[1,2-a]indol-9-amine Hydrochloride (I: R=3—OCH$_3$, R$^1$ and R$^2$=—CH$_3$, R$^3$ and R$^4$=—H)

Step (1) Preparation of N-(6,7,8,9-Tetrahydro-3-methoxy-10-methylpyrido[1,2-a]indol-9-yl)-N-methyl-formamide A mixture of formic acid (7 mL, 186 mmol) and acetic anhydride (14 mL, 148 mmol) was heated at 60° C. for 4 hours, then cooled to 0° C. and added to a solution of 6,7,8,9-tetrahydro-3-methoxy-N,10-dimethyl-pyrido[1,2-a]indol-9-amine hydrochloride (2 g, 8.2 mmol, described in Example 29, Step 6) in dry tetrahydrofuran (40 mL) at 0° C. The reaction mixture was stirred at 25° C. for 18 hours, then poured into water (50 mL) and extracted with ether (3×60 mL). The combined organic layers were washed with 5% hydrochloric acid (40 mL) and 5% sodium bicarbonate (3×40 mL). The organic layer was dried over MgSO$_4$, filtered, and evaporated to afford 2.23 g (99%) of the title amide as an amber oil.

NMR (clearly indicates the presence of two rotamers) δ1.75–2.38 (multiplets with singlet spike at 2.18, 7H, CH$_2$, CH$_3$—10), 2.71 and 2.82 (singlets, 3H, N—CH$_3$), 3.68–4.18 (multiplets with singlet spike at 3.89, 5H, CH$_2$—6, CH$_3$O), 4.95 and 5.89 (broad, 1H, H—9), 6.74–6.98 (m, 2H, H—2, H—4), 7.49 (d, 1H, H—1), 8.22 (br s, 1H, CHO);

MS (relative intensity, fragment) m/w 272 (33, M$^+$), 257 (6, M—CH$_3$), 243 (6, M—CHO), 214 (100, M—CH$_2$=N$^+$H—CHO).

Step (2) Preparation of 6,7,8,9-Tetrahydro-3-methoxy-N,N10-trimethylpyrido[1,2-a]indol-9-amine Hydrochloride A solution of N-(6,7,8,9-tetrahydro-3-methoxy-10-methylpyrido[1,2-a]indol-9-yl)-N-methyl-formamide (2 g, 7.4 mmol) in dry tetrahydrofuran (40 mL) was added dropwise to a suspension of lithium aluminum hydride (570 mg, 15 mmol) in the same solvent (50 mL). The reaction mixture was refluxed for 18 hours under exclusion of moisture, then cooled to 0° C. The metal complex was decomposed with 5% aqueous tetrahydrofuran (10 mL) under nitrogen. After stirring the mixture at 25° C. for 30 minutes, MgSO$_4$ was added, filtered, and evaporated to afford 1.72 g (90%) of the title amine as an amber oil.

NMR (CDCl$_3$) δ1.43–2.52 (multiplets with a singlet spike at 2.25, 13H, CH$_2$, CH$_3$—N—, CH$_3$—10), 3.57–4.31 (multiplets with a singlet spike at 3.87, 6H, CH$_2$—6, H—9, CH$_3$—O), 6.68–6.92 (m, 2H, H—2, H—4), 7.45 (d, 1H, H—1);

MS (relative intensity, fragment) m/e 258 (12, M$^+$), 214 (100, M—CH$_2$=N$^+$N—CH$_3$).

EXAMPLE 29

Preparation of 6,7,8,9-Tetrahydro-8,8,10-trimethylpyrido[1,2-a]indol-9-amine Hydrochloride A solution of 6,7,8,9-tetrahydro-8,8,10-trimethylpyrido[1,2-a]indol-9-ol (prepared in Example 1, step 4) (458 mg, 2 mmol) in dry pyridine (20 mL) was treated with methanesulfonyl chloride (458 mg, 4 mmol). The reaction mixture was stirred at ambient temperature for 2 hours, then saturated with dry ammonia gas at 25° C. Stirring was continued at 25° C. for 48 hours. The mixture was evaporated to near-dryness in vacuo. The residue was partitioned between ether (50 mL) and 5% NaHCO$_3$ (30 mL). The separated organic layer was extracted with 0.5N hydrochloric acid (30 mL). The aqueous layer was basified with saturated Na$_2$CO$_3$, then extracted with ether (3×20 mL). The combined extracts were dried over MgSO$_4$, filtered, and evaporated. The residue was chromatographed on neutral alumina (activity III). Ratio of alumina to residue 60:1. Elution with methylene chloride afforded 466 mg (88% yield) of the desired base. The hydrochloride salt was prepared in acetonitrile with ethereal hydrochloric acid, and crystallized from acetonitrile-ether, m.p. 214°–217° C.

NMR, 400 MHz (DMSO—d$_6$) δ0.88 and 1.22 (singlets, 3H+3H, CH$_3$—8), 1.69 (dd, J$_{gem}$=13.5 Hz, J=5.4 Hz, 1H, H—7), 2.29 (s, 3H, CH$_3$—10), 2.45 (m, 1H, H—7), 3.69 (td, J$_{gem}$=12 Hz, J=5.6 Hz, 1H, H—6ax), 4.27 (dd, J$_{gem}$=12 Hz, J=6.2 Hz, 1H, H—6 eq), 4.39 (br s, 1H, H—9), 7.07 (t, J=8.3 Hz, 1H, H—2), 7.19 (t, J=8.3 Hz, 1H, H—3), 7.41 (d, J=8.3 Hz, 1H, H—4), 7.54 (d, J=8.3 Hz, 1H, H—1), 8.3 (br, 3H, N$^+$H$_3$);

Anal. Calcd.: C, 68.04%; H, 7.99%; N, 10.58% Found: C, 67.89%; H, 8.11%; N, 10.56%.

EXAMPLE 30

Preparation of 2-Bromo-6,7,8,9-tetrahydro-8,8,10-trimethylpyrido[1,2-a]indol-9-amine Hydrochloride The title base was prepared from 2-bromo-6,7,8,9-tetrahydro-8,8,10-trimethylpyrido[1,2-a]indol-9-ol (prepared in Example 17, step (3) following the procedure described in Example 29.

The title hydrochloride salt was crystallized from acetonitrile-ether, m.p. 233°–236° C.

IR(KBr) 3420 (broad) cm$^{-1}$;

UV (MeOH) λ$_{max}$233 and 286 nm; ε=40,000 and 7,000 respectively;

NMR (DMSO-d$_6$) δ0.90 and 1.27 (singlets, 3H+3H, CH$_3$—8), 2.28 (s, 3H, CH$_3$—10), 4.32 (br s, 1H, H—9), 7.32 (m, 2H, H—3 and H—4), 7.70 (narrow doublet, 1H, H—1), 8.50 (br, 3H, NH$_3$);

MS (relative intensity, fragment) m/e 306 (53, M$^+$), 291 (100, M—CH$_3$), 289 (31, M—NH$_3$);

Anal. Calcd.: C, 52.41%; H, 5.87%; N, 8.15% Found: C, 52.20% H, 5.74%; N, 8.08%.

EXAMPLE 31

Preparation of N-Cyclopentyl-6,7,8,9-tetrahydro-8,8,10-trimethyl-pyrido[1,2-a]indol-9-amine Hydrochloride A solution of 6,7,8,9-tetrahydro-8,8,10-trimethylpyrido[1,2-a]indol-9-ol (prepared in Example 1, step 4) (458 mg, 2 mmol) in anhydrous pyridine (15 mL) was treated with methanesulfonyl chloride (458 mg, 4 mmol) under exclusion of moisture. The mixture was stirred at 25° C. for 2 hours. Cyclopentylamine (850 mg, 10 mmol) was added and stirring continued at 40° C. for 2 hours. The reaction mixture was evaporated to dryness, stripped with toluene (2×30 mL) and the residue partitioned between ether (50 mL) and 5% Na$_2$CO$_3$ (50 mL). The organic phase was separated and extracted with 0.5N hydrochloric acid (30 mL). The separated aqueous layer was washed with ether (50 mL), then basified with Na$_2$CO$_3$ and the product extracted with ether (2×40 mL). The combined extracts were separated, dried over MgSO$_4$, filtered, and evaporated to dryness. The residue was chromatographed on neutral alumina (activity III). Elution with methylene chloride/hexane (1:1) afforded 528 mg of the desired base. The hydrochloride salt was prepared in 89% yield in acetonitrile with ethereal HCl and crystallized from ethanol/ether, m.p. 179°–180° C.

IR (KBr) 3440 (very broad band) cm$^{-1}$;

UV (MeOH) λ$_{max}$277 nm (ε=7604);

NMR, (DMSO-d$_6$) δ0.80 and 1.37 (singlets, 3H+3H, CH$_3$—8), 1.44 and 1.72 (multiplets, 9H, CH$_2$ of cyclopentane and H—7), 2.30 (s, 3H, CH$_3$—10), 3.68 (m, 1H, H—6 ax), 4.30 (dd, J$_{gem}$=12 Hz, J=6.5 Hz, 1H, H—6 eq), 4.37 (d, J=5.5 Hz, 1H, H—9), 7.08 (t, J=8 Hz, 1H, H—2), 7.20 (t, J=8 Hz, 1H, H—3), 7.41 (d, J=8 Hz, 1H, H—4), 7.53 (d, J=8 Hz, 1H, H—1), 7.93 and 8.87 (broad, 1H+1H, N+H$_2$);

MS (relative intensity, fragment) m/e 296 (47, M+), 212 (100, loss of cyclopentylidene immonium);

Anal. Calcd.: C, 72.09%; H, 8.71%; N, 8.41% Found: C, 72.38%; H, 8.36%, N, 8.45%.

EXAMPLE 32

Preparation of N-Cyclohexyl-6,7,8,9-tetrahydro-N,8,8,10-tetramethyl-pyrido[1,2-a]indol-9-amine A solution of 6,7,8,9-tetrahydro-8,8,10-trimethyl-pyrido[1,2-a]indol-9-ol (prepared in Example 1, step 4) (458 mg, 2 mmol) in anhydrous pyridine (15 mL) was treated with methanesulfonyl chloride (458 mg, 4 mmol) and stirred at 25° C. for 2 hours. N-methylcyclohexylamine (1.36 g, 12 mmol) was added at 5° C. and stirring continued at 25° C. for 48 hours. The mixture was evaporated to near-dryness in vacuo and the residue partitioned between NaHCO$_3$ (20 mL) and ether (40 mL). The separated organic layer was extracted with 2% hydrochloric acid (3×10 mL). The aqueous solution was basified with saturated Na$_2$CO$_3$ and extracted with ether (3×20 mL). The combined organic extracts were dried over MgSO$_4$, filtered, and evaporated to dryness. The residue was chromatographed on neutral alumina (activity I). Elution with chloroform afforded 311 mg (48% yield) of the desired base, m.p. 108°-111° C. (ether) as a white powder.

IR (KBr) 3450 (very broad) cm$^{-1}$;

UV (MeOH) $\lambda_{max}$295, 288.5 and 230 nm; $\epsilon$=5500, 5600 and 21,815 respectively;

NMR, (CDCl$_3$) δ0.71 and 1.15 (singlets, 3H+3H, CH$_3$—8), 0.96-1.44 (multiplets, 10H, CH$_2$ of cyclohexane), 1.91 (s, 3H, CH$_3$—N), 2.26 (s, 3H, CH$_3$—10), 3.60 (d, J=1.8 Hz, 1H, H—9), 3.75 (td, J$_{gem}$=12.5 Hz, J=5.4 Hz, 1H, H—6 ax), 4.16 (dd, J$_{gem}$=12.5 Hz, J=6.2 Hz, 1H, H—6 eq), 7.06-7.26 (m, 3H, Ar—H), 7.53 (d, J=8 Hz, 1H, H—1);

MS (relative intensity, fragment) m/e 324 (10, M+) 212 (100, loss of C$_6$H$_{11}$—N+H=CH$_2$);

Anal. Calcd.: C, 81.43%; H, 9.94%; N, 8.63% Found: C, 81.29%; H, 9.84%; N, 8.54%.

EXAMPLE 33

Preparation of 6,7,8,9-Tetrahydro-2-hydroxy-8,8,10-trimethyl-9-(1-pyrrolidinyl)-pyrido[1,2-a]indole Hydrobromide A solution of 6,7,8,9-tetrahydro-2-methoxy-8,8,10-trimethyl-9-(1-pyrrolidinyl)-pyrido[1,2-a]indole (prepared in Example 15, step 5) (2.81 g, 9 mmol) in chloroform (54 mL) was cooled to 0° C. and treated under dry nitrogen with boron tribromide (5.62 g, 22.5 mmol). The mixture was stirred in the dark at 25° C. for 2 hours. Ethanol (54 mL) was added dropwise over 5 minutes at 0° C. Stirring was continued at 0°-5° C. for 1 hour. Ether (34 mL) was added slowly at 5° C. to induce crystallization. The obtained crystals were filtered, washed with ethanol/ether (2:1) and ether, then dried in vacuo at 65° C. affording 2.24 g (66% yield) of the title compound, m.p. 166°-170° C. as an off-white powder.

IR (KBr) broad bands at 3280 and 2970 cm$^{-1}$;

UV (MeOH) $\lambda_{max}$281 and 311 nm; $\epsilon$=10,315 and 4,927 respectively;

NMR, (DMSO-d$_6$) δ0.77 and 1.38 (singlets, 3H+3H, CH$_3$—8), 2.21 (s, 3H, CH$_3$—10), 4.79 (narrow doublet, 1H, H—9), 6.75 (dd, J$_o$=8 Hz, J$_m$=1.8 Hz, 1H, H—3), 6.85 (d, J$_m$=1.8 Hz, 1H, H—1), 7.26 (d, J$_o$=8 Hz, 1H, H—4), 8.77 and 8.90 (broad exchangeable peaks, 2H, NH+ and OH);

MS m/e 298 and 228;

Anal. Calcd.: C, 60.16%; H, 7.17%; N, 7.38%; Found: C, 60.35%; H, 7.27%; N, 7.48%.

The compounds of formula I have been subjected to pharmaceutical tests which demonstrated protection against anoxia-induced lethality in mice and prevention of scopolamine-induced memory impairment in rats.

Anoxia-induced Lethality Test in Mice

The anoxia-induced lethality test in mice evaluates the activity of drugs which protect the animal from deleterious effects of oxygen-lack, such as occurs in conditions of cerebral ischemia. Activity is measured as the survival rate in mice exposed to 100% nitrogen for 80 seconds, a procedure which is lethal to 95% of untreated animals.

Test compounds are dissolved in water, or suspended in 0.2% aqueous Tween 80 and are administered i.p., 30 minutes prior to testing. Several doses and a vehicle control are tested, with 8 mice receiving each dose.

Male, CD-1 mice weighing 18-20 g are used. Mice are held separately within a cage in a modified plastic, air-tight desiccator which is connected to a tank of compressed 100% nitrogen gas.

Delivery of the anoxic gas is controlled by means of a toggle valve, and exposure is terminated by rapidly removing the mice from the desiccator. All operations are timed with a stopwatch. An ED$_{50}$ value is determined from the percentage of mice which survive in each group. Drugs which reduce the anoxia-induced lethality solely by lowering body temperature are excluded.

| PROTECTION FROM ANOXIA-INDUCED LETHALITY IN MICE | |
|---|---|
| Example # | ED$_{50}$ (mg/kg i.p.) |
| 3, 20, 21 | 13.5 |
| 19 | 109.5 |
| 8 | 55.7 |
| 2 | 83.3 |
| 9 | 32.4 |
| 7 | 22.0 |
| 27 | 15.1 |
| 28 | 20.0 |
| 29 | 17.2 |
| 1 | 11.2 |
| 4 | 5.0 |
| 6 | 20.0 |
| 17 | 50.0 |
| 32 | 8.8 |
| 33 | 20.0 |

Passive Avoidance Test

The present compounds have been also evaluated for their ability to prevent scopolamine-induced memory impairment in rats by means of a passive avoidance procedure.

This passive avoidance procedure uses a test chamber divided into two compartments: a lighted compartment and a dark compartment.

The two compartments are separated by a solenoid-operated slide door. An inescapable foot shock (750 μA for two seconds) can be presented to the grid floor of the dark compartment.

On the training day, male Sprague-Dawley rats (eight animals are tested per group) are placed in the lighted compartment and given access to the adjacent dark compartment. Upon entering the dark compartment, the rat is given an inescapable foot shock. Twenty-four hours later retention (memory) is tested: the rat is placed in the lighted compartment and allowed access to the dark compartment for 180 seconds. Vehicle treated control rats do not enter the dark compartment; however, rats injected with scopolamine (2.0 mg/kg s.c.) 15 or 30 minutes prior to the training session, enter the dark compartment during the retention test within 50 seconds.

Compounds to be tested are dissolved in 0.9% saline or suspended in Tween 80 (0.2% v/v in saline) or methyl cellulose (0.5% w/v in distilled water). The test compounds are administered orally in a volume of 1 mL/kg, 75 or 90 minutes prior to training the animals for the passive avoidance response; scopolamine is then given subcutaneously at 2 mg/kg, 15 or 30 minutes prior to the training session. Appropriate vehicle and control groups are included with each experiment. Each animal is given a single training trial.

Active compounds induce a significant increase in the entry latency (100–150 seconds depending on the control) on retention day. For example, 6,7,8,9-tetrahydro-10-methyl-9-(1-pyrrolidinyl)-pyrido[1,2-a]indole (30 mg/kg) of Example 2 and 6,7,8,9-tetrahydro-8,8,10-trimethyl-9-(1-pyrrolidinyl)-pyrido[1,2-a]indole (30 mg/kg) of Example 1 produced mean entry latencies 135 and 152 seconds, respectively.

We claim:

1. The process for the production of compounds having the structure (I)

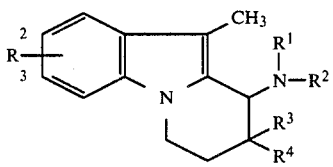
(I)

wherein R is hydrogen, lower alkyl, halogen, alkoxy containing 1 to 4 carbon atoms, hydroxy, $R^1$ and $R^2$ are independently selected from the group consisting of hydrogen, lower alkyl, cycloalkyl containing 3 to 7 carbon atoms, alkynyl containing 2 to 4 carbon atoms, or, $R^1$ and $R^2$ are joined together to form a heterocyclic amine radical, selected from the group consisting of pyrrolidinyl, piperidinyl and morpholinyl, and $R^3$ and $R^4$ represent hydrogen, lower alky, or alkenyl, wherein lower alkyl and lower alkenyl contain 1 to 4 carbon atoms, wherein comprises (a) dialkylating the compound of structure V

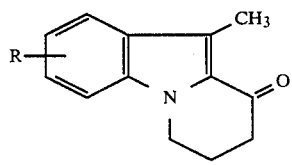
(V)

wherein R is as defined above with an alkyl halogenide in the presence of a strong base to obtain the compound of structure VI

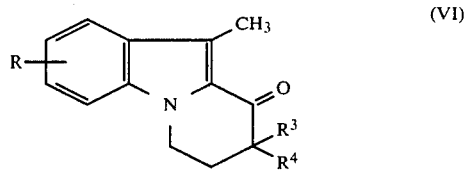
(VI)

wherein R, $R^3$ and $R^4$ are as defined above (b) reducing said compound of structure VI to obtain the compound of structure VII

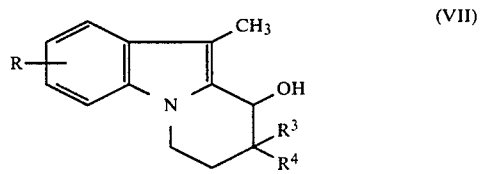
(VII)

wherein R, $R^3$ and $R^4$ are as defined above (c) treating said structure VII with mesy, tosyl or thionyl chloride in the presence of base, at a temperature of about 0° C. to 70° C., to obtain the compound of structure VIII

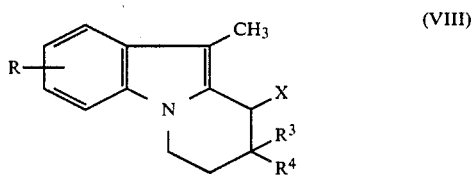
(VIII)

wherein R, $R^3$ and $R^4$ are as defined above and X is halogen, $-OSO_2-CH_3$, and

and (d) treating said structure VIII with the amine $R^1R^2NH$ wherein $R^1$ and $R^2$ are as defined above, at a temperature of about 0° C. to about 70° C.

2. The process according to claim 1 wherein $R^3$ and $R^4$ are both not hydrogen.

3. The process for preparing compounds of formula I

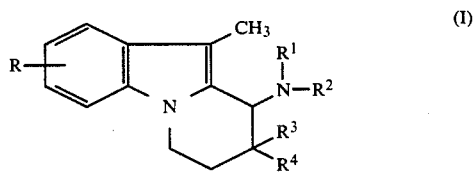
(I)

wherein R is hydrogen, lower alkyl, halogen, alkoxy containing 1 to 4 carbon atoms, hydroxy, $R^1$ and $R^2$ are lower alkyl and $R^3$ and $R^4$ represent hydrogen which comprises.

(a) reacting the compound of formula V

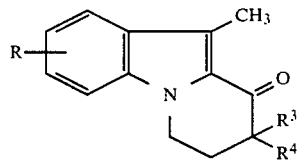

wherein R, $R^3$ and $R^4$ are as defined above with hydroxylamine hydrochloride in the presence of base to produce the compound of formula IX

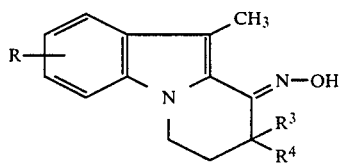

wherein R, $R^3$ and $R^4$ are as defined above (b) reducing the compound of formula IX to produce the compound of formula X

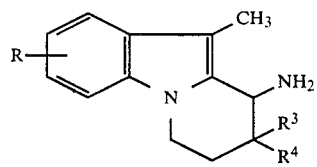

wherein R, $R^3$ and $R^4$ are as defined above (c) acylating said compound of formula X to produce the compound of formula XI

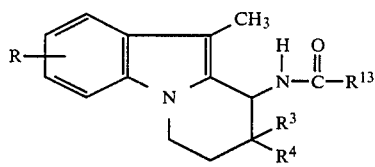

wherein R, $R^3$ and $R^4$ are as defined above and $R^{13}$ is selected to make —$CH_2$—$R^{13}$ equal to $R^1$ wherein $R^1$ is lower alkyl (d) alkylating said compound of formula XI with alkyl halogenide in the presence of sodium hydride to produce the compound of formula XIV

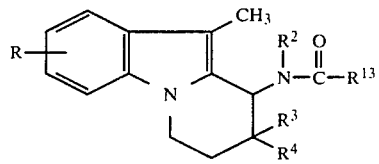

wherein R, $R^2$, $R^3$, $R^4$ and $R^{13}$ are as defined above and reducing said compound of formula XIV.

4. The process according to claim 3 for preparing compounds of formula I

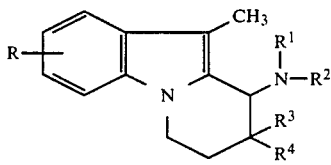

wherein R is hydrogen, lower alkyl, halogen, alkoxy containing 1 to 4 carbon atoms, hydroxy, $R^1$ and $R^2$ are lower alkyl and $R^3$ and $R^4$ represent hydrogen, which comprises (a) reducing the compound of formula XI

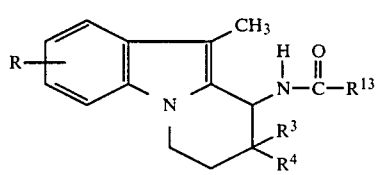

wherein R, $R^3$ and $R^4$ are as defined above and $R^{13}$ is selected to make —$CH_2$—$R^{13}$ equal to $R^1$ wherein $R^1$ is lower alkyl to produce the compound of formula XII

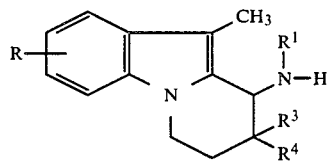

wherein R, $R^1$, $R^3$ and $R^4$ are as defined above (b) acylating the compound of formula XII to produce the compound of formula XIII

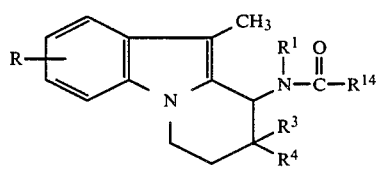

wherein R, $R^1$, $R^3$ and $R^4$ are as defined above and $R^{14}$ is selected to make —$CH_2$—$R^{14}$ equal to $R^2$ wherein $R^2$ is lower alkyl and reducing said compound of formula XIII.

* * * * *